US011440870B2

(12) United States Patent
Mechoulam et al.

(10) Patent No.: US 11,440,870 B2
(45) Date of Patent: Sep. 13, 2022

(54) CANNABIDIOLIC ACID ESTERS COMPOSITIONS AND USES THEREOF

(71) Applicants: Yissum Research Development Company of the Hebrew University of Jerusalem Ltd., Jerusalem (IL); University of Guelph, Guelph (CA)

(72) Inventors: Raphael Mechoulam, Jerusalem (IL); Linda Parker, Campbell River (CA); Roger Pertwee, Scotland (GB); Aron Weller, Shoham (IL); Joseph Tam, Jerusalem (IL); Christeen Haj, Nazareth Hit (IL); Reem Smoum, Jerusalem (IL)

(73) Assignees: UNIVERSITY OF GUELPH, East Guelph (CA); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/343,050

(22) PCT Filed: Jun. 20, 2018

(86) PCT No.: PCT/IL2018/050678
§ 371 (c)(1),
(2) Date: Apr. 18, 2019

(87) PCT Pub. No.: WO2018/235079
PCT Pub. Date: Dec. 27, 2018

(65) Prior Publication Data
US 2020/0115317 A1    Apr. 16, 2020

Related U.S. Application Data

(60) Provisional application No. 62/522,243, filed on Jun. 20, 2017.

(51) Int. Cl.
*C07C 69/94*    (2006.01)
*A61P 25/22*    (2006.01)
*A61P 1/08*    (2006.01)
*C07C 69/28*    (2006.01)

(52) U.S. Cl.
CPC ............... *C07C 69/94* (2013.01); *A61P 1/08* (2018.01); *A61P 25/22* (2018.01); *C07C 69/28* (2013.01)

(58) Field of Classification Search
CPC ........................................... A61K 31/05
USPC ........................................ 514/544
See application file for complete search history.

(56) References Cited

U.S. PATENT DOCUMENTS

| | | | |
|---|---|---|---|
| 5,342,971 A | 8/1994 | Herlt et al. | |
| 6,166,066 A | 12/2000 | Makriyannis | |
| 7,759,526 B2 | 7/2010 | Mechoulam | |
| 9,670,133 B2 | 6/2017 | Koch | |
| 9,701,618 B2 | 7/2017 | Appendino et al. | |
| 9,962,341 B2 | 5/2018 | Stott | |
| 2010/0298579 A1 | 11/2010 | Steup et al. | |
| 2015/0336874 A1* | 11/2015 | Koch | C07C 67/29 514/544 |
| 2018/0244642 A1 | 8/2018 | Koch | |

FOREIGN PATENT DOCUMENTS

| | | |
|---|---|---|
| CN | 106810426 A | 6/2017 |
| EP | 2842933 B1 | 7/2015 |
| EP | 2314580 B1 | 9/2015 |
| EP | 3041815 B1 | 4/2019 |
| GB | 1517590 A | 7/1978 |
| JP | 2009510078 A | 3/2009 |
| WO | 2006002050 A1 | 1/2006 |
| WO | 2011110866 A1 | 9/2011 |
| WO | 2013038157 A1 | 3/2013 |
| WO | 2014202990 A1 | 12/2014 |
| WO | 2015158381 A1 | 10/2015 |
| WO | 2015198071 A1 | 12/2015 |
| WO | 2016059411 A1 | 4/2016 |
| WO | 2018002637 A1 | 1/2018 |
| WO | 2018235079 A1 | 12/2018 |
| WO | 2019234728 A1 | 12/2019 |

OTHER PUBLICATIONS

Ahmed et al., (2008) Cannabinoid Ester Constituents from High-Potency *Cannabis sativa*. J Nat Prod. Author manuscript; available in PMC May 27, 2016. 18 pages.
Hen-Shoval et al., (2018) Acute oral cannabidiolic acid methyl ester reduces depression-like behavior in two genetic animal models of depression. Behav Brain Res 351: 1-3.
Ligresti et al., (2006) Antitumor activity of plant cannabinoids with emphasis on the effect of cannabidiol on human breast carcinoma. J Pharmacol Exp Ther 318(3): 1375-1387.
Mass et al., (2004) Antitumor effects of cannabidiol, a non psychoactive cannabinoid, on human glioma cell lines. J Pharmacol Exp Ther 308(3): 838-845.
Alexander et al., (2017) The Concise Guide to Pharmacology 2017/18: G protein-coupled receptors. Br J Pharmacol 174 Suppl 1:S17-S129.

(Continued)

*Primary Examiner* — Ana Z Muresan
(74) *Attorney, Agent, or Firm* — Rothwell, Figg, Ernst & Manbeck, P.C.

(57) ABSTRACT

Cannabidiolic acid esters, compositions comprising them and uses thereof in the treatment of various diseases, conditions and symptoms.

7 Claims, 15 Drawing Sheets

(56) References Cited

OTHER PUBLICATIONS

Bluett et al., (2014) Central anandamide deficiency predicts stress-induced anxiety: behavioral reversal through endocannabinoid augmentation. Transl Psychiatry 4: e408; 5 pages.
Bolognini et al., (2013) Cannabidiolic acid prevents vomiting in Suncus murinus and nausea-induced behaviour in rats by enhancing 5-HT1A receptor activation. Br J Pharmacol 168(6): 1456-1470.
Campos and Guimarães (2008) Involvement of 5HT1A receptors in the anxiolytic-like effects of cannabidiol injected into the dorsolateral periaqueductal gray of rats. Psychopharmacology (Berl) 199(2): 223-230.
Cascio et al., (2010) Evidence that the plant cannabinoid cannabigerol is a highly potent $\alpha$2-adrenoceptor agonist and moderately potent 5HT1A receptor antagonist. Br J Pharmacol 159(1): 129-141.
Christopoulos et al., (2014) International Union of Basic and Clinical Pharmacology. XC. multisite pharmacology recommendations for the nomenclature of receptor allosterism and allosteric ligands. Pharmacol Rev 66(4): 918-947.
Crombie and Crombie (1977) Cannabinoid acids and esters: miniaturized synthesis and chromatographic study. Phytochemistry 16(9): 1413-1420.
Curtis et al., (2015) Experimental design and analysis and their reporting: new guidance for publication in BJP. Br J Pharmacol 172(14): 3461-3471 with erratum.
Grill and Norgren (1978) Chronically decerebrate rats demonstrate satiation but not bait shyness. Science 201(4352): 267-269.
Kilkenny et al., (2010) Animal research: reporting in vivo experiments: the ARRIVE guidelines. Br J Pharmacol 160(7): 1577-1579.
Krejčí and Šantavý (1955) Isolace dalších látek z listí indického konopí*Cannabis sativa* L.. Acta Univ Palacki Olomuc 6: 59-66. With English summary of the study.
Laprairie et al., (2015) Cannabidiol is a negative allosteric modulator of the cannabinoid CB1 receptor. Br J Pharmacol 172(20): 4790-4805.
Limebeer et al., (2010) Inverse agonism of cannabinoid CB1 receptors potentiates LiCl-induced nausea in the conditioned gaping model in rats. Br J Pharmacol 161(2): 336-349.
McGrath and Lilley (2015) Implementing guidelines on reporting research using animals (ARRIVE etc.): new requirements for publication in BJP. Br J Pharmacol 172(13): 3189-3193.
Mechoulam and Ben-Zvi Z (1969) Carboxylation of resorcinols with methylmagnesium carbonate. Synthesis of cannabinoid acids. J Chem Soc D 0: 343 344.
Mechoulam and Gaoni (1965) Hashish. IV. The isolation and structure of cannabinolic cannabidiolic and cannabigerolic acids. Tetrahedron 21(5): 1223-1229.
Mechoulam et al., (2002) Cannabidiol: an overview of some pharmacological aspects. J Clin Pharmacol 42(S1): 11S-19S.
Patel et al., (2017) The endocannabinoid system as a target for novel anxiolytic drugs. Neurosci Biobehav Rev 76(Pt A): 56-66.

Petrzilka et al., (1969) Synthese von Haschisch-Inhaltsstoffen. 4. Mitteilung. 52(4): 1102-1134. Abstract.
Rock and Parker (2013) Effect of low doses of cannabidiolic acid and ondansetron on LiCl-induced conditioned gaping (a model of nausea-induced behaviour) in rats. Br J Pharmacol 169(3): 685-692.
Rock and Parker (2015) Synergy between cannabidiol, cannabidiolic acid, and $\Delta^9$-tetrahydrocannabinol in the regulation of emesis in the *Suncus murinus* (house musk shrew). Behav Neurosci 129(3): 368-370.
Rock et al., (2008) The effect of cannabidiol and URB597 on conditioned gaping (a model of nausea) elicited by a lithium-paired context in the rat Psychopharmacology (Berl) 196(3): 389-395.
Rock et al., (2012) Cannabidiol, a non-psychotropic component of cannabis, attenuates vomiting and nausea-like behaviour via indirect agonism of 5-HT(1A) somatodendritic autoreceptors in the dorsal raphe nucleus. Br J Pharmacol 165(8): 2620-2634.
Rock et al., (2014) A comparison of cannabidiolic acid with other treatments for anticipatory nausea using a rat model of contextually elicited conditioned gaping. Psychopharmacology (Berl) 231(16): 3207-3215.
Rock et al., (2015) Effect of combined doses of $\Delta(9)$-tetrahydrocannabinol (THC) and cannabidiolic acid (CBDA) on acute and anticipatory nausea using rat (Sprague-Dawley) models of conditioned gaping. Psychopharmacology (Berl) 232(24): 4445-4454.
Rock et al., (2016) Effect of combined oral doses of $\Delta(9)$-tetrahydrocannabinol (THC) and cannabidiolic acid (CBDA) on acute and anticipatory nausea in rat models. Psychopharmacology (Berl) 233(18): 3353-3360.
Rock et al., (2017) Effect of prior foot shock stress and $\Delta 9$-tetrahydrocannabinol, cannabidiolic acid, and cannabidiol an anxiety-like responding in the light-dark emergence test in rats Psychopharmacology (Berl) 234(14): 2207-2217.
Shoyama et al., (1977) Cannabis. X. The Isolation and Structures of Four New Propyl Cannabinoid Acids, Tetrahydrocannabivarinic Acid, Cannabidivarinic Acid, Cannabichromevarinic Acid and Cannabigerovarinic Acid, from Thai Cannabis, 'Meao Variant'. Chemical & pharmaceutical bulletin 25(9): 2306-2311.
Southan et al., (2016) The IUPHAR/BPS Guide to Pharmacology in 2016: towards curated quantitative interactions between 1300 protein targets and 6000 ligands. Nucleic Acids Res 44(D1): D1054 D1068.
Takeda et al., (2014) Down-regulation of cyclooxygenase-2 (COX-2) by cannabidiolic acid in human breast cancer cells. J Toxicol Sci 39(5): 711-716.
Takeda et al., (2017) Cannabidiolic acid-mediated selective down-regulation of c-fos in highly aggressive breast cancer MDA-MB-231 cells: possible involvement of its down-regulation in the abrogation of aggressiveness. J Nat Med 71 (1): 286-291.
Zhornitsky and Potvin (2012) Cannabidiol in humans-the quest for therapeutic targets. Pharmaceuticals (Basel) 5(5): 529-552.
Zuardi et al., (1993) Effects of ipsapirone and cannabidiol on human experimental anxiety. J Psychopharmacol 7(1 Suppl): 82-88.

\* cited by examiner

CANNABIDIOLIC ACID ESTERS COMPOSITIONS AND USES THEREOF

BACKGROUND OF THE INVENTION

Cannabidiolic acid (CBDA) is a major constituent of *Cannabis sativa*. It was first isolated in 1955 (Krejčí and Šantavý, 1955) and its structure was elucidated in 1965 by analysis of the physical properties of its methyl ester (Mechoulam and Gaoni, 1965). Its synthesis from cannabidiol was subsequently reported (Mechoulam and Ben-Zvi, 1969).

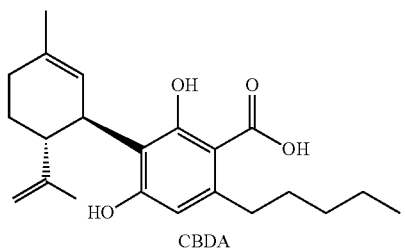 [SMILES: C=C(C)[C@@H]1CCC(C)=C[C@H]1c1c(O)cc(CCCCC)c(C(=O)O)c1O]

CBDA

Cannabidiolic acid (CBDA) gradually decarboxylates, while still in the plant, to cannabidiol (Mechoulam, 1973), a process that is speeded up by heat. Whereas cannabidiol has been the topic of a large number of publications, and its biological/therapeutic properties have now been reasonably well identified (Mechoulam et al., 2002; Zhornitsky & Potvin, 2012; Cascio and Pertwee, 2014), our knowledge of the pharmacology of cannabidiolic acid is much more limited.

The limited amount of information on this phyto-cannabinoid that has been published suggests that it may have a wide variety of actions and effects. Accordingly, it has been shown to inhibit breast cancer cell migration (Takeda et al., 2017) and to cause down-regulation of cyclooxygenase-2 (COX-2) (Takeda et al., 2014). Recent evidence suggests that CBDA (at a dose as low as 1 µg·kg$^{-1}$ i.p.) can induce potent 5-HT$_{1A}$ receptor-mediated anti-nausea effects as indicated by its apparent ability to prevent both vomiting in *Suncus murinus* and acute nausea-induced behavior of conditioned gaping in rats (Grill & Norgren, 1978) by enhancing 5-HT$_{1A}$ receptor activation (Bolognini et al., 2013; Rock et al., 2013; 2015b). As well as reducing acute nausea, CBDA has the potential to reduce anticipatory (conditioned) nausea, an effect experienced by chemotherapy patients upon returning to the clinic in which they received their nauseating treatment (Rock et al., 2014; 2015a; 2016). There are currently no effective selective treatments for anticipatory nausea once it develops in such patients. It is noteworthy, therefore, that Rock et al, (2014; 2015a; 2016) have demonstrated that CBDA reduces contextually-elicited conditioned gaping (a model of anticipatory nausea), also by a 5-HT$_{1A}$ dependent mechanism of action. Finally, like CBD, CBDA has also been shown to produce anxiolytic-like effects under conditions of high stress at doses as low as 0.1 µg·kg$^{-1}$, i.p (Rock et al., 2017).

However, CBDA is highly instable, especially when subjected to heat. Hence, there was a growing need to find an analogue of CBDA, having higher stability. It was surprisingly found by the inventors of the present application that ester derivatives of CBDA provided both the sought-after stability, but also similar or more effective biological profile than CBDA.

SUMMARY OF THE INVENTION

The invention thus provides a compound having the general formula (I):

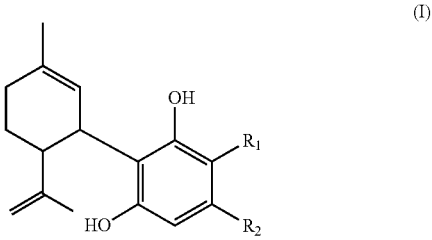

Wherein, $R_1$ is selected from —C(=O)OR$_3$, —OC(=O)R$_4$; $R_2$ is selected from a straight or branched $C_1$-$C_{15}$ alkyl, straight or branched $C_2$-$C_{15}$ alkenyl and straight or branched $C_2$-$C_{15}$ alkynyl; each independently optionally substituted by at least one substituent selected from hydroxy (—OH), halogen, amine and amide or any combinations thereof; $R_3$ and $R_4$ are each independently selected from a straight or branched $C_1$-$C_{15}$ alkyl, straight or branched $C_2$-$C_{15}$ alkenyl, straight or branched $C_2$-$C_{15}$ alkynyl (said alkyl, alkenyl or alkynyl are each optionally substituted with by at least one substituent selected from hydroxy (—OH), halogen, amine and amide or any combinations thereof), halogen, amine and amide.

The invention further provides a compound having the general formula (II):

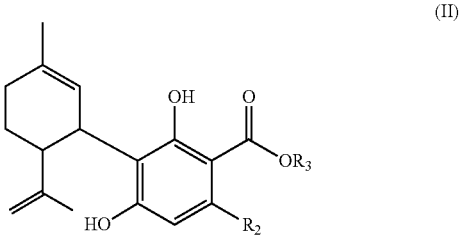

Wherein, $R_2$ is selected from a straight or branched $C_1$-$C_{15}$ alkyl, straight or branched $C_2$-$C_{15}$ alkenyl and straight or branched $C_2$-$C_{15}$ alkynyl; each independently optionally substituted by at least one substituent selected from hydroxy, halogen, amine and amide or any combinations thereof; $R_3$ is selected from a straight or branched $C_1$-$C_{15}$ alkyl, straight or branched $C_2$-$C_{15}$ alkenyl, straight or branched $C_2$-$C_{15}$ alkynyl (said alkyl, alkenyl or alkynyl are each optionally substituted with by at least one substituent selected from hydroxy (—OH), halogen, amine and amide or any combinations thereof), halogen, amine and amide.

In some embodiments, $R_2$ is a straight or branched $C_1$-$C_{15}$ alkyl. In other embodiments, $R_2$ is a straight or branched $C_2$-$C_{15}$ alkenyl. In further embodiments, $R_2$ is a straight or branched $C_2$-$C_{15}$ alkynyl.

In some embodiments, $R_3$ is a straight or branched $C_1$-$C_{15}$ alkyl. In other embodiments, $R_3$ is a straight or branched $C_2$-$C_{15}$ alkenyl. In further embodiments, $R_3$ is a straight or branched $C_2$-$C_{15}$ alkynyl. In yet further embodiments, $R_3$ is selected from a halogen, an amine and an amide. In some embodiments, $R_3$ being an alkyl, alkenyl or alkynyl is optionally substituted with by at least one substituent selected from hydroxy (—OH), halogen, amine and amide or any combinations thereof.

In some embodiments, a compound of the present invention is HU-580:

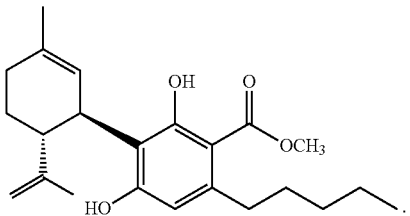

HU-580

The invention further provides a compound having the general formula (III):

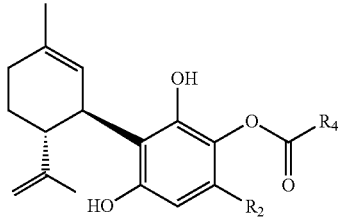

(III)

Wherein, $R_2$ is selected from a straight or branched $C_1$-$C_{15}$ alkyl, straight or branched $C_2$-$C_{15}$ alkenyl and straight or branched $C_2$-$C_{15}$ alkynyl; each independently optionally substituted by at least one substituent selected from hydroxy, halogen, amine and amide or any combinations thereof; $R_4$ is selected from a straight or branched $C_1$-$C_{15}$ alkyl, straight or branched $C_2$-$C_{15}$ alkenyl, straight or branched $C_2$-$C_{15}$ alkynyl (said alkyl, alkenyl or alkynyl are each optionally substituted with by at least one substituent selected from hydroxy (—OH), halogen, amine and amide or any combinations thereof), halogen, amine and amide.

The term "halogen" means F, Cl, Br or I.

The term "amine" as used herein refers to an —NRR'R" radical, wherein each of R, R' and R" is selected from H, straight or branched $C_1$-$C_{15}$ alkyl, straight or branched $C_2$-$C_{15}$ alkenyl and straight or branched $C_2$-$C_{15}$ alkynyl.

The term "amide" as used herein refers to an —C(=O) NRR'R" or —NRC(=O)R' radical, wherein each of R, R' and R" is selected from H, straight or branched $C_1$-$C_{15}$ alkyl, straight or branched $C_2$-$C_{15}$ alkenyl and straight or branched $C_2$-$C_{15}$ alkynyl.

The term "$C_1$-$C_{15}$ alkyl" as used herein represents a saturated, branched or straight hydrocarbon group having 1, 2, 3, 4, 5, 6, 7, 8, 9, 10, 11, 12, 13, 14 or 15 carbon atoms all connected via sigma bonds.

The term "$C_2$-$C_{15}$ alkenyl" as used herein represents a branched or straight hydrocarbon group having 2, 3, 4, 5, 6, 7, 8, 9, 10, 11, 12, 13, 14 or 15 carbon atoms, wherein at least one of the bonds connecting said carbon atoms is a double bond, all other bonds may be of any other type (single and/or double).

The term "$C_2$-$C_{15}$ alkynyl" as used herein represents a branched or straight hydrocarbon group having 2, 3, 4, 5, 6, 7, 8, 9, 10, 11, 12, 13, 14 or 15 carbon atoms, wherein at least one of the bonds connecting said carbon atoms is a triple bond, all other bonds may be of any other type (single and/or double and/or triple).

As used herein, the term "optional substituent" denotes that the corresponding substituent may be present or may be absent. Accordingly, a compound of the invention may have 1, 2, 3 or more optional substituents at any point of the radical that is defined as having this optional substitution.

It is to be understood that the compounds provided herein may contain one or more chiral centers. Such chiral centers may each be of either of the (R) or (S) configuration. In case a compound of the invention contains more than one chiral center, each one of those chiral centers may be of the (R) or (S) configuration, independently. Thus, the compounds provided herein may be enantiomerically pure, or be stereoisomeric or diastereomeric mixtures.

The invention further provides a composition comprising at least one compound as defined herein above and below, of general formula (I) and (II).

In a further aspect, the invention provides a compound as defined herein above and below, of general formula (I) and (II), for use in the treatment of a condition, disease or symptom associated with 5-$HT_{1A}$ receptor.

In a further aspect, the invention provides a compound as defined herein above and below, of general formula (I) and (II), for use in the treatment of a condition, disease or symptom selected from nausea, vomiting, convulsions and any combinations thereof.

In a further aspect, the invention provides a compound as defined herein above and below, of general formula (I) and (II), for use in the treatment of a condition, disease or symptom associated with depression.

In a further aspect, the invention provides a compound as defined herein above and below, of general formula (I) and (II), for use in the treatment of a condition, disease or symptom selected from anxiety, stress, depression, schizophrenia, panic, withdrawal syndrome, auto-immune disease, inflammation, reduction of infarct size, increase blood flow in stroke, obesity, metabolic syndrome, retinopathy, nausea, myocardia, liver, renal ischemic/reperfusion injury, neuronal damage, Huntington's disease, Alzheimer's disease, cerebral infarction, hepatic encephalopathy, traumatic brain injury, cerebral ischemia, spinal cord injury, memory rescuing effects, cancer, angiogenesis, epilepsy, convulsions, neuropathic pain, airway obstruction, obsessive-compulsive behavior, cognitive impairment, impaired sexual drive and function, sleep disturbance, opioid-related respiratory suppression, addiction and any combinations thereof.

By another aspect the present invention concerns a method of treating a disease, the disease characterized by being improved by cannabidiolic acid (CBDA), the method comprising: administering to a subject in need of such treatment a therapeutically effective amount of a compound as defined herein above and below, of general formula (I) and (II).

Non-limiting examples of disease, conditions and symptoms are: Anxiety and stress, Depression, Schizophrenia, Panic and anxiety, Withdrawal symptoms in *cannabis* and tobacco addiction, reward-facilitating effect of morphine and cocaine, Auto-immune diseases of any type (diabetes type 1, GVHD being specific non-limiting examples), Inflammation (Crohn's disease, colitis, pancreatitis, rheumatoid arthritis), Reduction of infarct size and increase blood flow in stroke, obesity (treated by reduced food consumption; or by lowering appetite), metabolic syndrome, retinopathy associated with diabetes, nausea, myocardial, liver, renal ischemic/reperfusion injury, neuronal damage (due to neurological diseases or injury, Parkinson's disease, Huntington's disease, Alzheimer's disease, cerebral infarction, hepatic encephalopathy, traumatic brain injury, cerebral ischemia, spinal cord injury, memory rescuing effects, cancer and resistance to cancer chemotherapy, cancer cell migration (metastasis), angiogenesis, epilepsy and convulsions, chronic inflammatory and neuropathic pain, airway obstruction, Obsessive-compulsive behavior and any combinations thereof.

In some embodiments, the diseases conditions and symptoms are selected from nausea (both anticipatory and acute), vomiting, anxiety and affective disorders of any type, such as depression (including major depression, mild depression and bipolar disease).

The present invention concerns a method for the treatment of a disease wherein a clinical beneficial effect is evident by the activation of $5HT_{1A}$ receptors the method comprising administering to a subject in need of such treatment an effective amount of at least one compound of general formula (I) or (II).

Non-limiting examples of such diseases and conditions are: hypertension, anxiety, vomiting and nausea, pain, Schizophrenia, Parkinson's disease, cognitive impairment, impaired sexual drive and function, obesity (the effect is suppressed food consumption), sleep disturbance (in particular short rem duration), opioid-related respiratory suppression, addiction and any combinations thereof.

In particular, the diseases that show an improved clinical outcome, due to $5HT_{1A}$ activation are nausea (both anticipatory and acute) and vomiting (anti emetic and anti-nausea), anxiety and affective disorder of any type, mainly depression (including major depression, mild depression and bipolar disease) and any combinations thereof.

Thus, when referring herein to a "condition, symptom or disease associated with $5HT_{1A}$ receptor" it should be understood to include hypertension, anxiety, vomiting and nausea, pain, Schizophrenia, Parkinson's disease, cognitive impairment, impaired sexual drive and function, obesity (the effect is suppressed food consumption), sleep disturbance (in particular short rem duration), opioid-related respiratory suppression, addiction, nausea (both anticipatory and acute) and vomiting (anti emetic and anti-nausea), anxiety and affective disorder of any type, mainly depression (including major depression, mild depression and bipolar disease) and any combinations thereof.

By another aspect the present invention concerns a method for the treatment of a disease selected from: a nausea (both anticipatory and acute), anxiety and affective disorder of any type, mainly depression (including major depression, mild depression and bipolar disease); the method comprising: administering to a subject in need of such treatment an effective amount of CBDA-ME.

In another one of its aspects the invention provides a compound as disclosed herein above and below for use in the treatment of at least one disease, condition, symptom or disorder associated with kidney dysfunction. The invention further provides a method of treating at least one disease, condition, symptom or disorder associated with kidney dysfunction in a patient in need thereof; said method comprising administering to said patient at least one compound of the present invention.

When referring to "kidney dysfunction" in the context of the present application, it should be understood to include any type (qualitative or quantitative) of reduction or failure of kidney function and may be acute or chronic. Such kidney dysfunction may be caused by any reason including injury, disease, genetic disposition and so forth. Causes of acute kidney dysfunction include, but are not limited to low blood pressure, blockage of the urinary tract, medications, muscle breakdown, hemolytic uremic syndrome, and any combinations thereof. Additional causes of chronic kidney dysfunction include, but are not limited to diabetes, high blood pressure, nephrotic syndrome, polycystic kidney disease and any combinations thereof.

In some embodiments, such diseases, conditions, symptoms and disorders that are associated with kidney dysfunction include, but are not limited to diabetic nephropathy, chronic and acute kidney injuries, chronic and acute kidney diseases, acute-on-chronic kidney failure, obesity-associated kidney damage, and any combinations thereof.

Conditions and symptoms associated with kidney dysfunction include but are not limited to: high levels of urea in the blood, vomiting, diarrhea, nausea, weight loss, nocturnal urination, changes in urination frequency and quantity, blood in the urine, pressure, or difficulty urinating, buildup of phosphates in the blood, itching, bone damage, nonunion in broken bones, muscle cramps, buildup of potassium in the blood, abnormal heart rhythms, muscle paralysis, failure of kidneys to remove excess fluid, swelling of the legs, ankles, feet, face, or hands, shortness of breath, polycystic kidney disease, large fluid-filled cysts on the kidneys, pain in the back or side, lowering production of erythropoietin, decreased production of red blood cells, anemia, foamy or bubbly urine, swelling in the hands, feet, abdomen, or face, appetite loss, excess protein in the blood and urine, seizures when administered with high doses of penicillin and any combinations thereof.

The present invention also relates to pharmaceutical compositions comprising a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy. Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The invention further provides a method of treating a condition, disease or symptom associated with $5\text{-}HT_{1A}$ receptor; said method comprising administering to a patient in need thereof at least one compound disclosed herein or above (compounds of formula (I), (II) and so forth).

The invention further provides a method of treating a condition, disease or symptom selected from nausea, vomiting, convulsions and any combinations thereof; said method comprising administering to a patient in need thereof at least one compound disclosed herein or above (compounds of formula (I), (II) and so forth).

The invention further provides a method of treating a condition, disease or symptom associated with depression; said method comprising administering to a patient in need thereof at least one compound disclosed herein or above (compounds of formula (I), (II) and so forth).

The invention further provides a method of treating a condition, disease or symptom selected from anxiety, stress, depression, schizophrenia, panic, withdrawal syndrome, auto-immune disease, inflammation, reduction of infarct size, increase blood flow in stroke, obesity, metabolic syndrome, retinopathy, nausea, myocardia, liver, renal ischemic/reperfusion injury, neuronal damage, Huntington's disease, Alzheimer's disease, cerebral infarction, hepatic encephalopathy, traumatic brain injury, cerebral ischemia, spinal cord injury, memory rescuing effects, cancer, angiogenesis, epilepsy, convulsions, neuropathic pain, airway obstruction, obsessive-compulsive behavior, cognitive impairment, impaired sexual drive and function, sleep disturbance, opioid-related respiratory suppression, addiction and any combinations thereof; said method comprising administering to a patient in need thereof at least one compound disclosed herein or above (compounds of formula (I), (II) and so forth).

The invention further provides a method of treating at least one disease, condition, symptom or disorder associated with kidney dysfunction; said method comprising administering to a patient in need thereof at least one compound disclosed herein or above (compounds of formula (I), (II) and so forth).

As used herein, the term "treating a disease, disorder, condition or symptom" refers to a slowing of, or a reversal of, the progress of the disease, disorder or symptom thereof. Treating a disease or disorder includes treating a symptom and/or reducing the symptoms of the disease.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
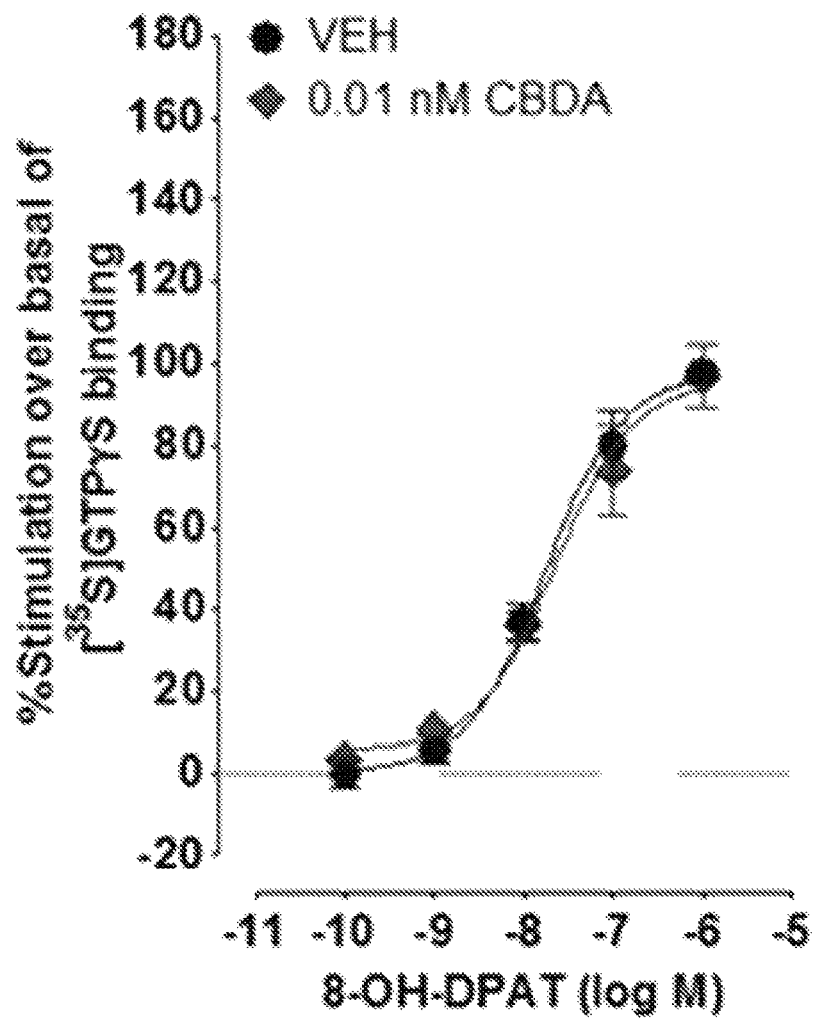
FIGS. 1A-1E show the effect of CBDA (0.01, 0.1, 1.0, 10 or 100 nM) on 8-OH-DPAT-induced stimulation of [$^{35}$S]-GTPγS binding to membranes obtained from CHO cells stably transfected with human $5\text{-}HT_{1A}$ receptors. Symbols represent mean values±SEM (n=6). Mean $E_{max}$ and $EC_{50}$ values for 8-OH-DPAT determined in the presence of CBDA or just of its vehicle (VEH), DMSO, together with the 95% confidence limits of these values, are listed in Table 1.
Figure 1B:
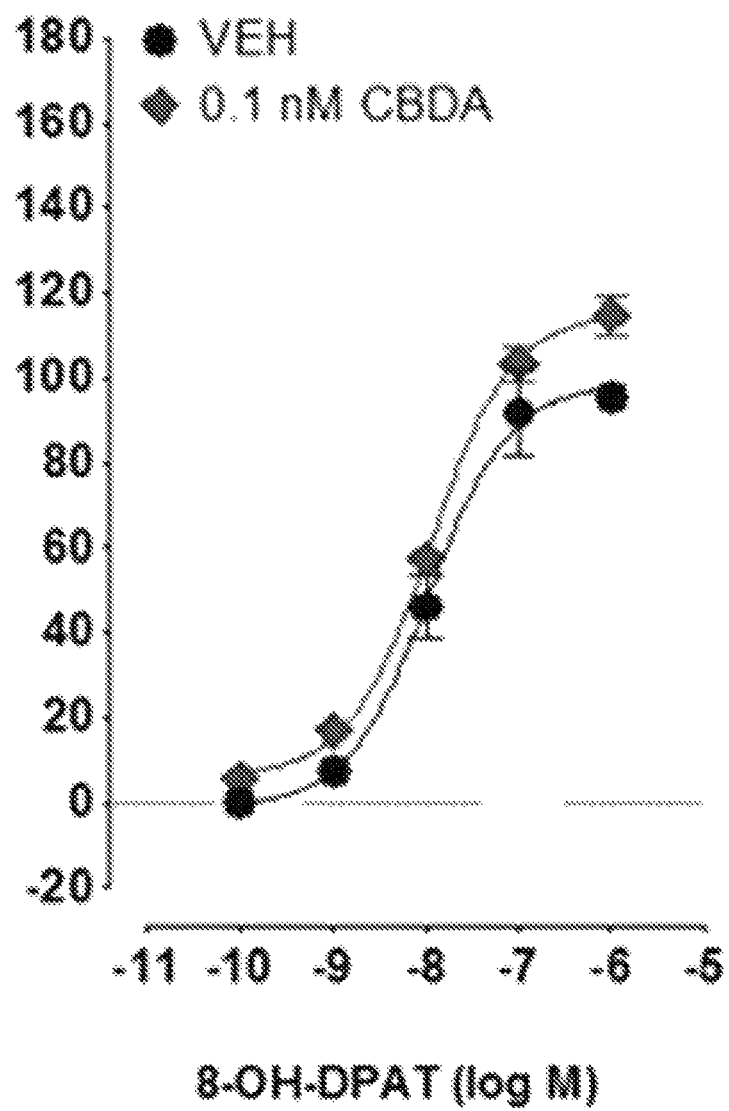
Figure 1C:
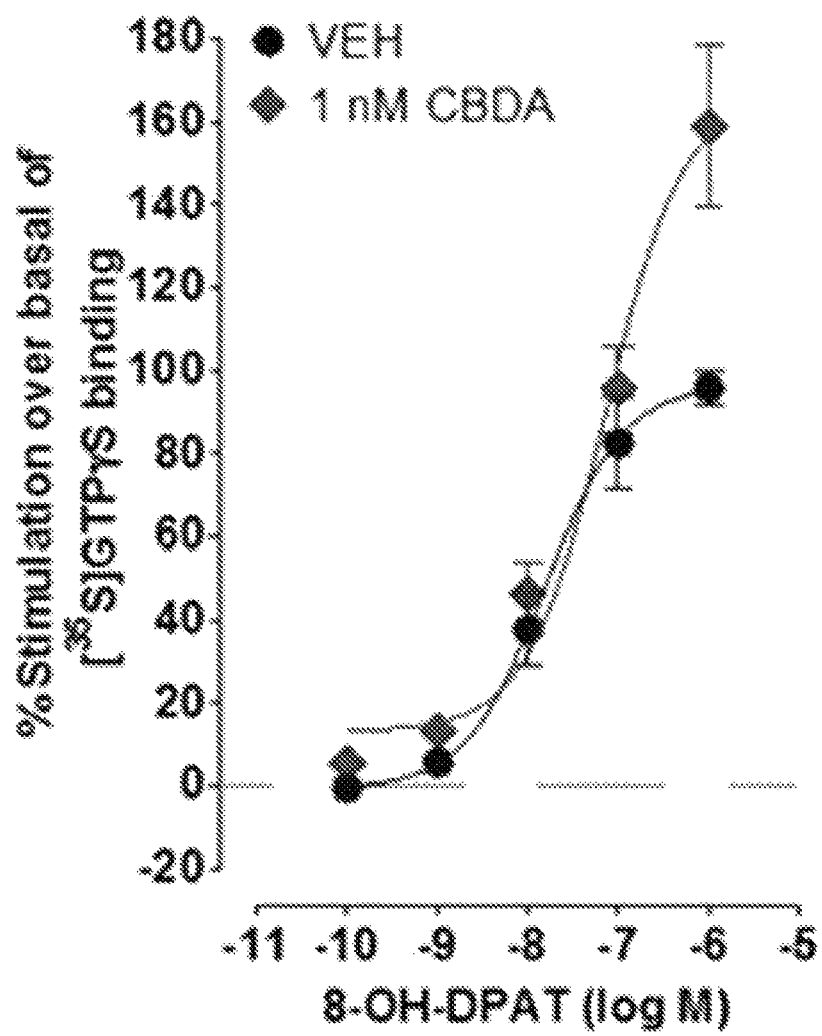
Figure 1D:
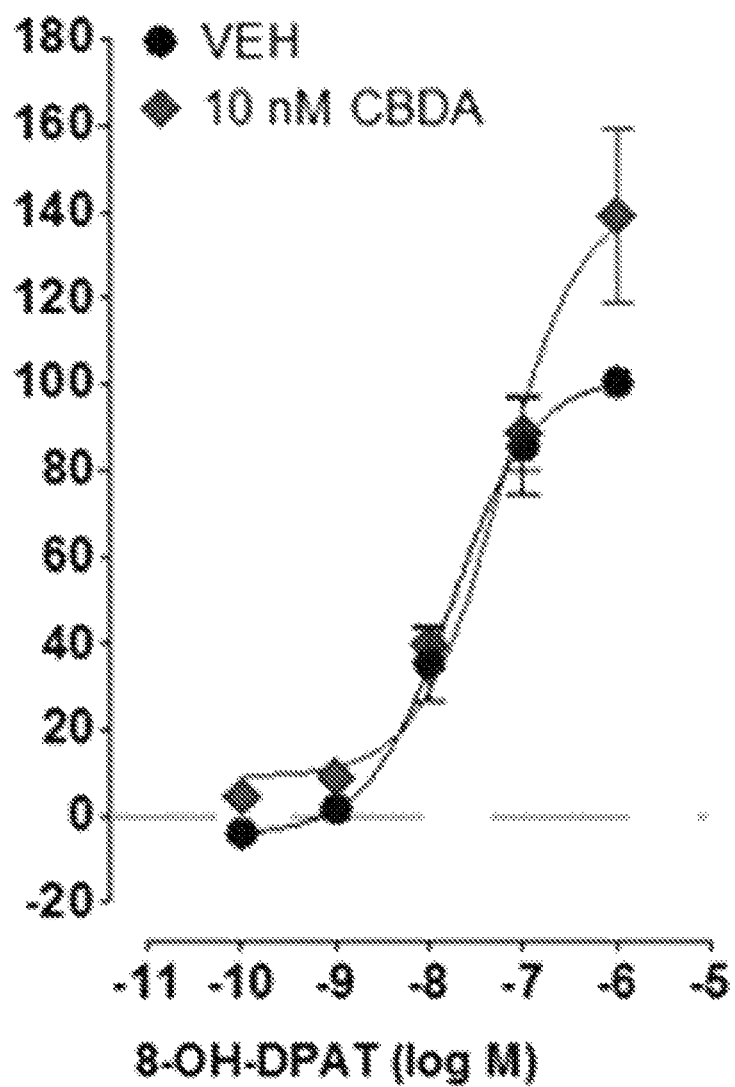
Figure 1E:
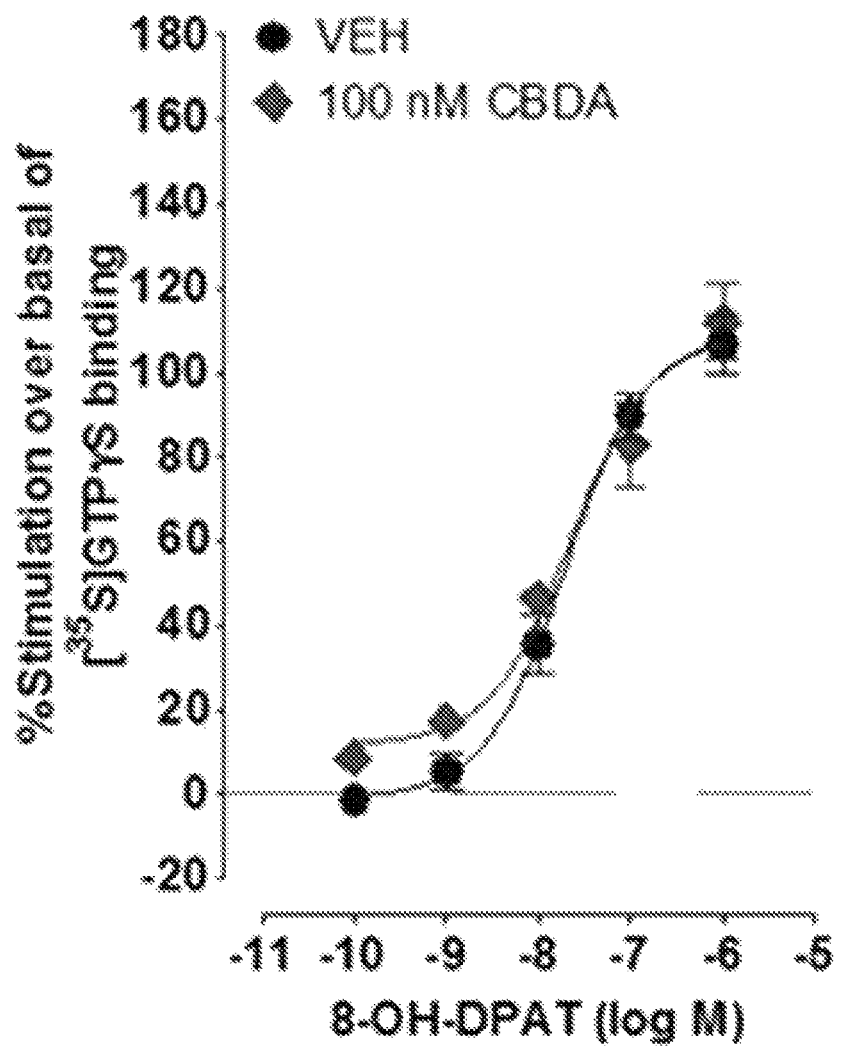
Figure 2A:
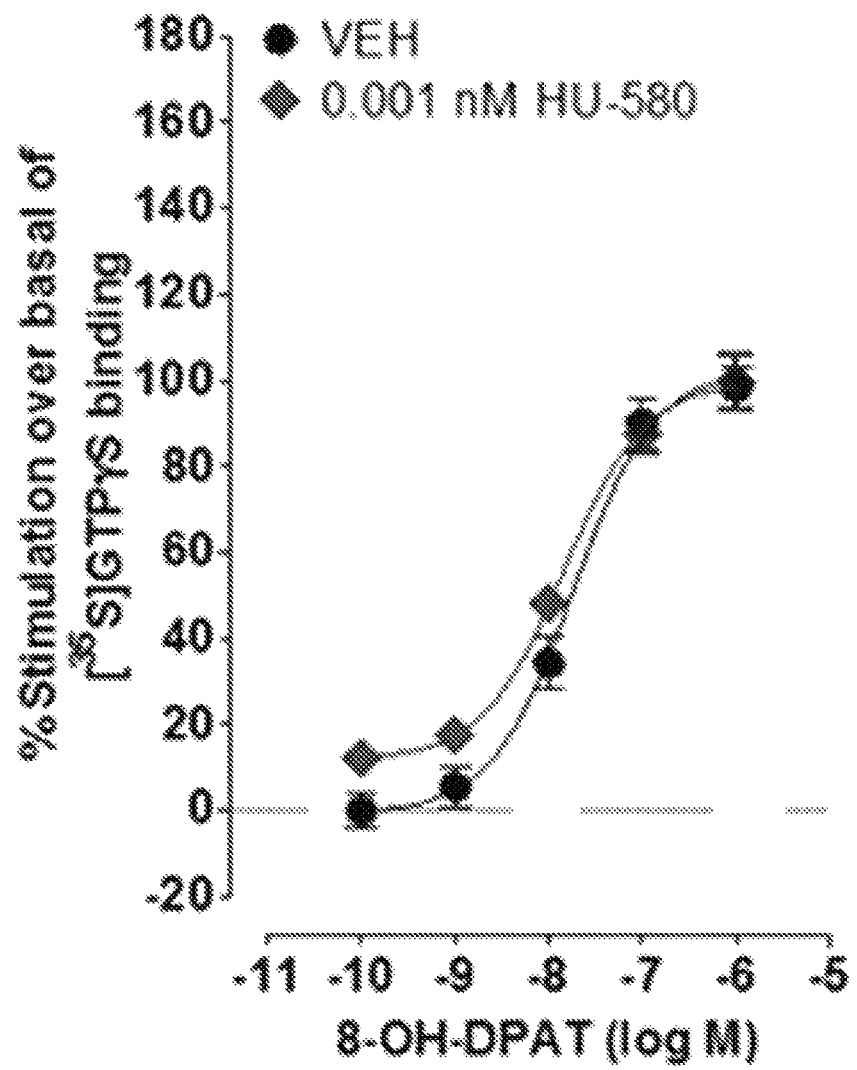
FIGS. 2A-2F show the effect of HU-580 (0.001, 0.01, 0.1, 1.0, 10 or 100 nM) on 8-OH-DPAT-induced stimulation of [$^{35}$S]-GTPγS binding to membranes obtained from CHO cells stably transfected with human $5\text{-}HT_{1A}$ receptors. Symbols represent mean values±SEM (n=6). Mean $E_{max}$ and $EC_{50}$ values for 8-OH-DPAT determined in the presence of HU-580 or just of its vehicle (VEH), DMSO, together with the 95% confidence limits of these values, are listed in Table 2.
Figure 2B:
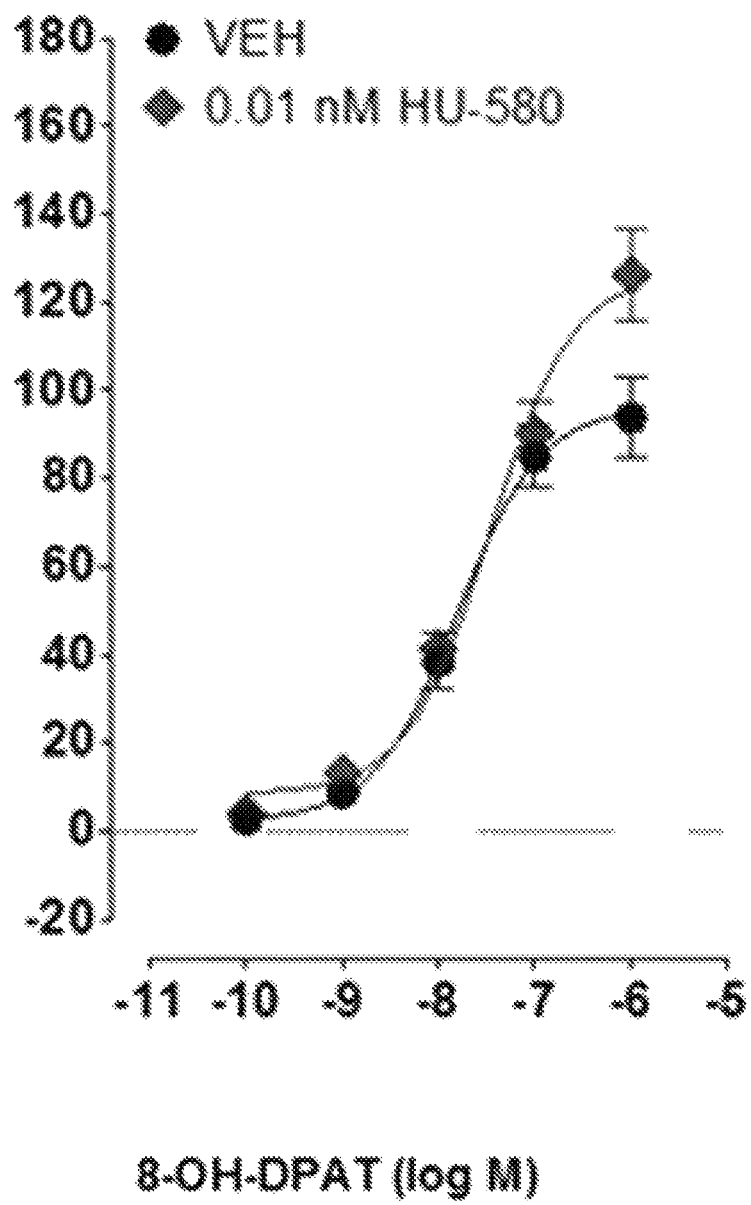
Figure 2C:
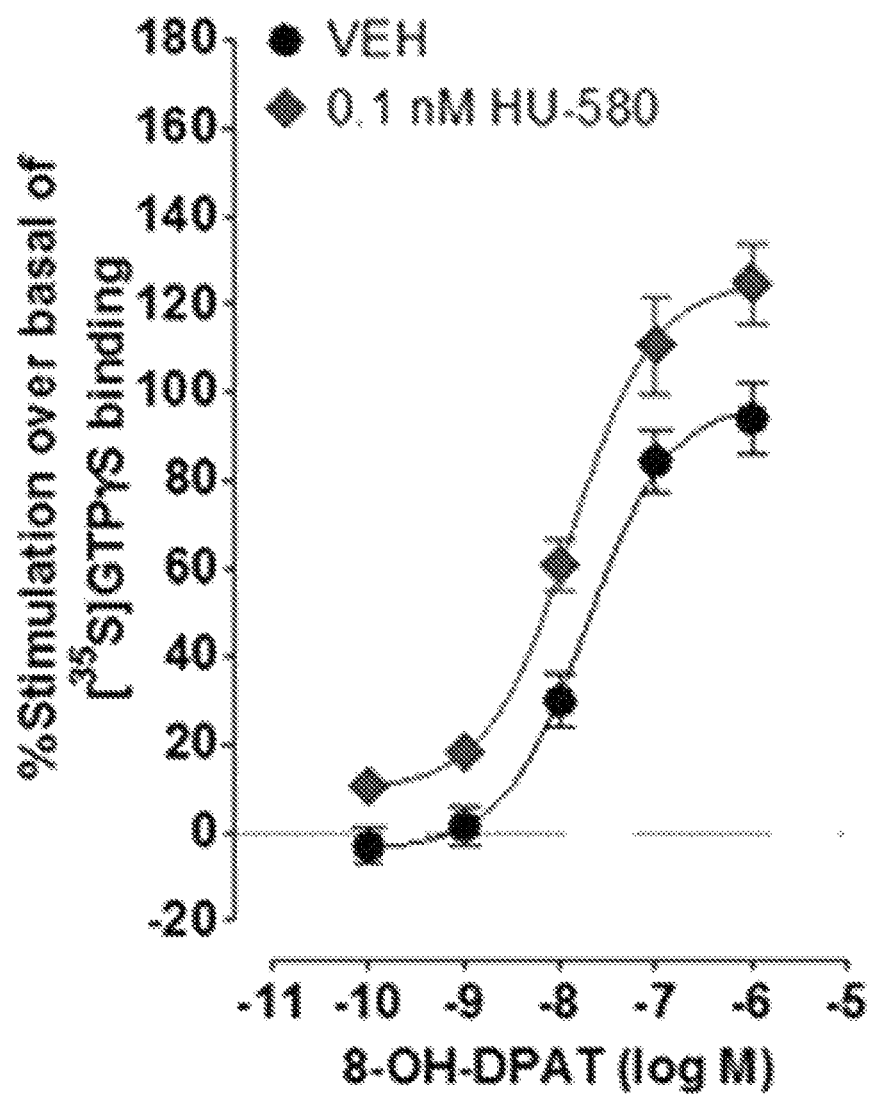
Figure 2D:
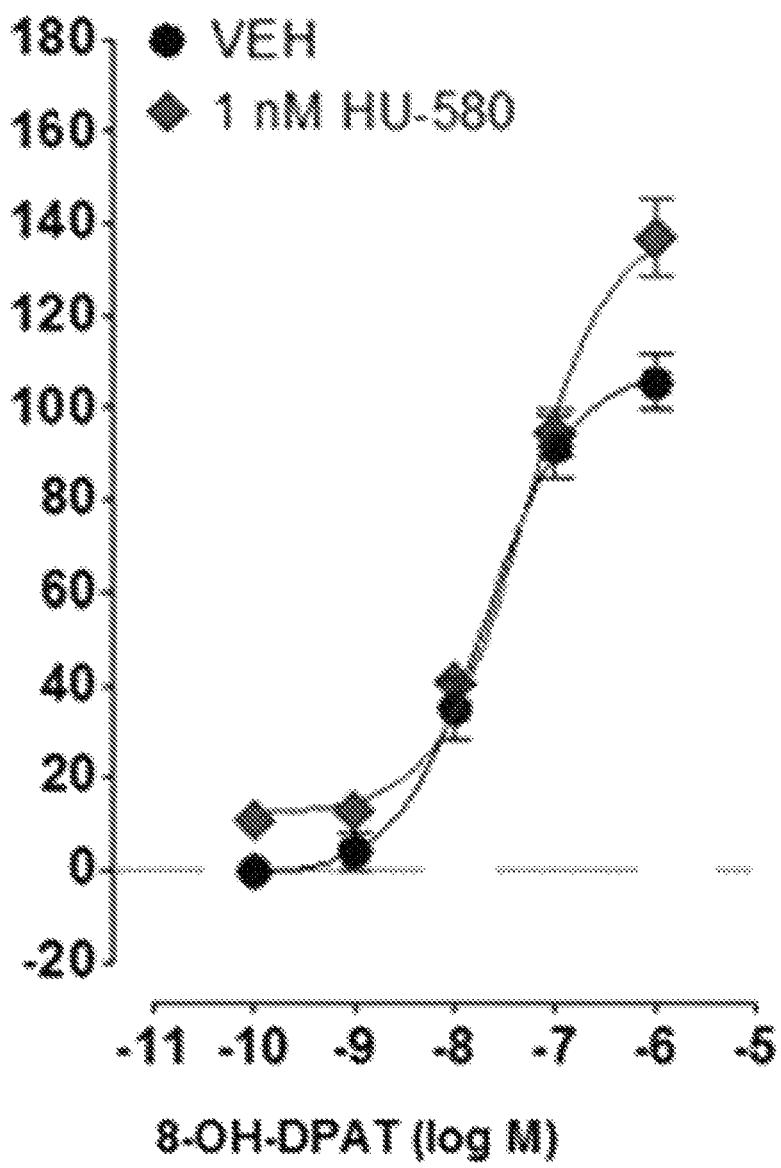
Figure 2E:
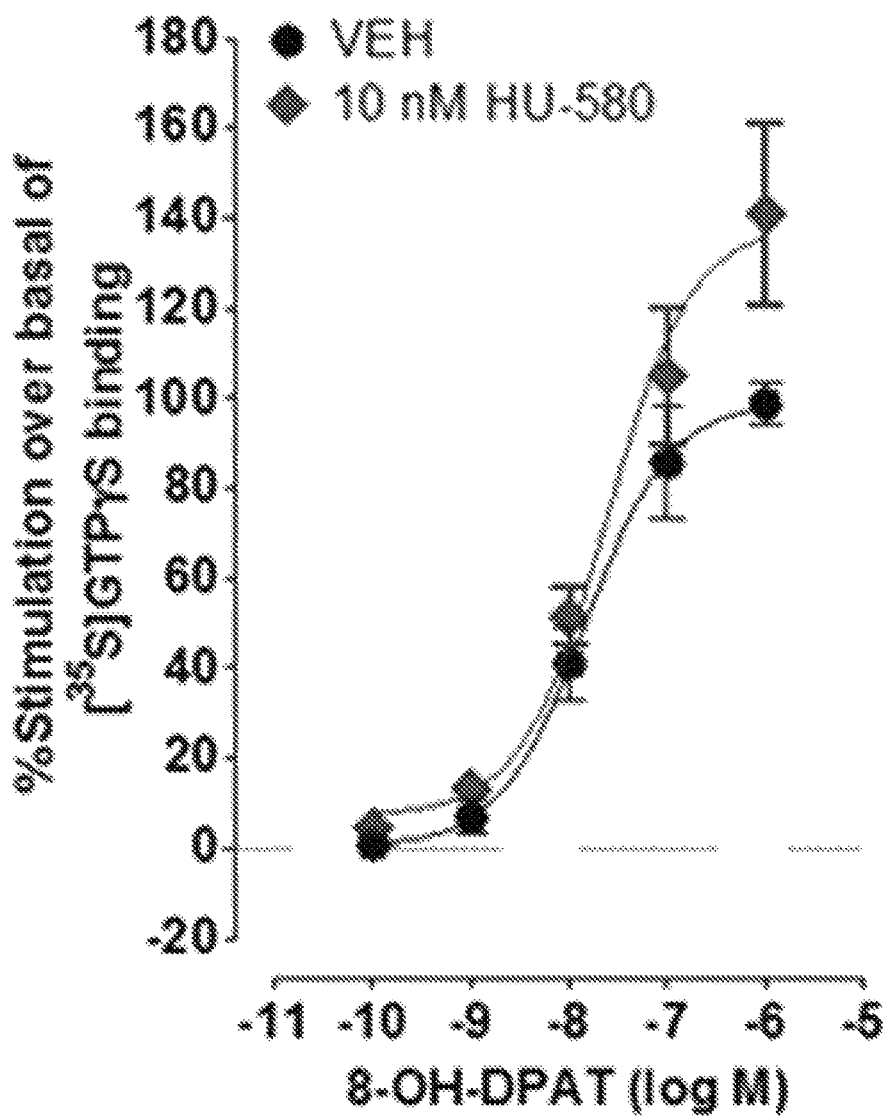
Figure 2F:
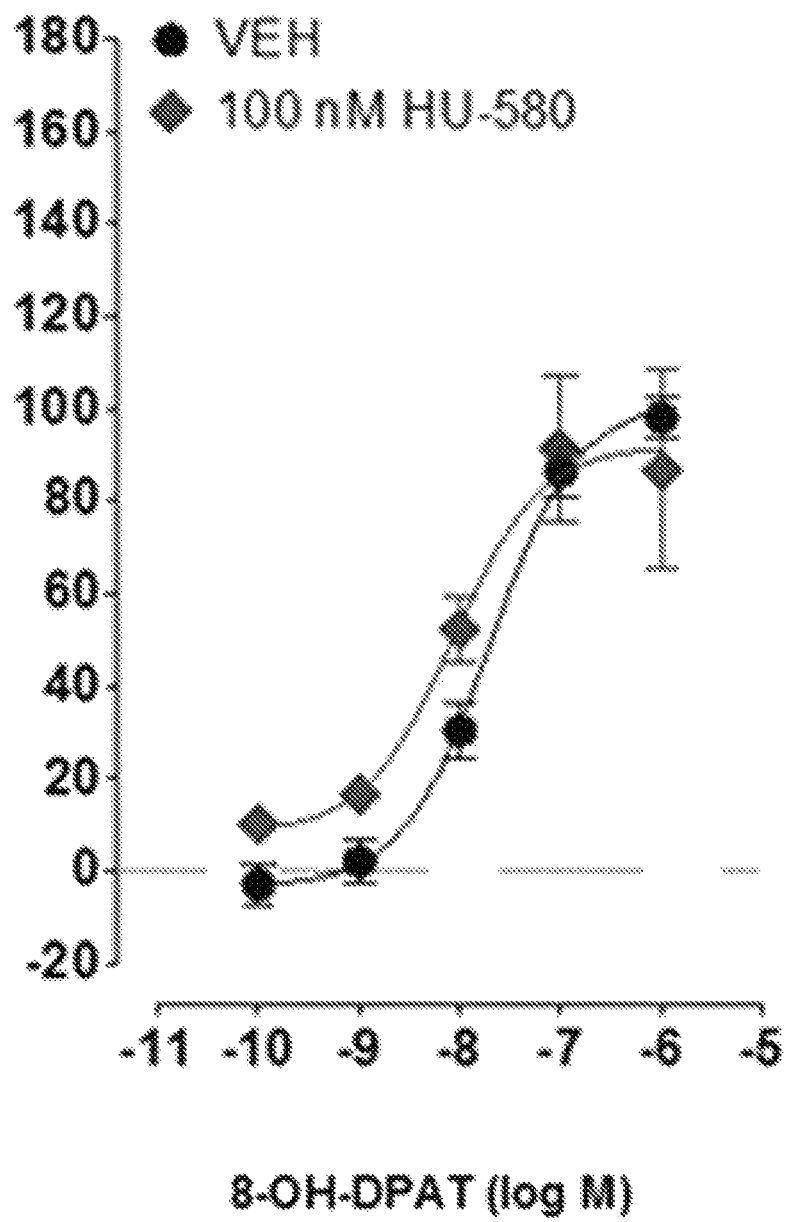

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Synthesis

Synthesis of Cannabidiolic Acid (CBDA):

A mixture of Cannabidiol (CBD, 314 mg, 1 mmol) and 2 molar solution of Magnesium Methyl Carbonate (MMC/2M, 1.5 ml, 3 mmol) in dimethylformamide (DMF) is heated at 130° C. for 3 hours. Then the reaction is cooled to 0° C., acidified with 10% hydrochloric acid and extracted with ether. The organic layer is washed with saline, dried over the drying agent magnesium sulfate ($MgSO_4$) and then evaporated. The crude compound is then cleaned by column chromatography (20% ether-petroleum ether).

Synthesis of Cannabidiolic Acid Methyl Ester (HU-580):

To a solution of Cannabidiolic Acid (CBDA) (175 mg, 0.488 mmol) in 2.5 ml dichloromethane ($CH_2Cl_2$), add 0.02 ml of methanol ($CH_3OH$, 0.488 mmol) and 7.2 mg of 4-Pyrrolidinopyridine (0.048 mmol). The reaction is stirred for 5 minutes at room temperature followed by the addition of the coupling agent, N,N'-Dicyclohexylcarbodiimide (DCC) (121 mg, 0.585 mmol) and stirred overnight. Then the solvent was evaporated and the crude mixture acidified with 5% hydrochloric acid and extracted with dichloromethane ($CH_2Cl_2$). The organic layer is washed with saturated aqueous sodium bicarbonate ($NaHCO_3$), dried over the drying agent magnesium sulfate ($MgSO_4$) and then evaporated. The crude compound is then cleaned by column chromatography (2% ether-petroleum ether).

$^1$H-NMR spectra were obtained using a Bruker AMX 300 MHz apparatus using the deuterated DMSO. Thin-layer chromatography (TLC) was run on silica gel 60$F_{254}$ plates (Merck). Column chromatography was performed on silica gel 60 Å (Merck). Compounds were located using a UV lamp at 254 nm. GCMS analyses were performed on an HP GCMS instrument (Model GCD PLUS) with an EI detector and 30 m methyl silicone column.

$^1$H NMR (300 MHz, (($CD_3$)$_2$SO)) δ 6.18 (1H, s, Ar), 5.07 (1H, s), 4.44 (1H, s), 4.41 (1H, s), 3.82 (3H, s), 3.35 (1H, m), 2.66 (1H, m), 2.49 (2H, t), 2.09 (1H, b), 1.95 (3H, s), 1.71-1.05 (12, ms), 0.86 (3H, t). GC MS=314 m/z.

Biological Methods

In Vitro Procedures

Cho Cells.

CHO cells stably transfected with cDNA encoding human 5-$HT_{1A}$ receptors (a generous gift from Dr Keith Parker) were maintained at 37° C. and 5% $CO_2$ in Gibco™ Ham's F-12 Nutrient Mix supplied by Fisher Scientific UK Ltd that was supplemented both with 2 mM L-glutamine, 10% FBS and 0.6% penicillin-streptomycin, all also supplied by Fisher Scientific UK Ltd, and with the disulphate salt of G418 [(2R,3S,4R,5R,6S)-5-amino-6-{[(1R,2S,3S,4R,6S)-4,6-diamino-3-{[(2R,3R,4R,5R)-3,5-dihy-droxy-5-methyl-4-(methylamino)oxan-2-yl]oxy}2-hydroxy cyclohexyl]oxy}-2-[(1R)-1-hydroxyethyl]oxane-3,4-diol; 600 mg·mL$^{-1}$] supplied by Sigma-Aldrich UK.

[$^{35}$S]-GTPγS binding assay. Each assay was carried out with human 5-$HT_{1A}$ CHO cell membranes (50 μg protein per well), GTPγS-binding buffer (50 mM Tris-HCl; 50 mM Tris-Base; 5 mM $MgCl_2$; 1 mM EDTA; 100 mM NaCl; 1 mM DTT and 0.1% BSA), 0.1 nM [$^{35}$S]-GTPγS and 30 μM GDP, in a final volume of 500 μL (Cascio et al., 2010). Binding was initiated by the addition of [$^{35}$S]-GTPγS to the wells. Non-specific binding was measured in the presence of 30 μM GTPγS. Assays were performed at 30° C. for 60 min (Cascio et al., 2010). The reaction was terminated by a rapid vacuum filtration method using Tris-binding buffer as described previously by Cascio et al. (2010), and the radioactivity was quantified by liquid scintillation spectrometry. In all the [$^{35}$S]-GTPγS-binding assays, 0.1 nM [$^{35}$S]-GTPγS was used, 30 mM GDP and a protein concentration of 5 μg per well. CBDA, HU-580, 8-OH-DPAT and WAY100635 were stored at −20° C. as 10 mM stock solutions dissolved in DMSO.

In Vivo Procedures

Animals.

Animal procedures complied with the Canadian Council on Animal Care, and the protocols were approved by the Institutional Animal Care Committee at University of Guelph. Animal studies are reported in compliance with the ARRIVE guidelines (Kilkenny et al., 2010; McGrath and Lilley, 2015). A total of 200 näive male Sprague-Dawley rats, obtained from Charles River Laboratories (St Constant, Quebec), were used for all in vivo studies. Rats were individually housed (for acute nausea studies) or pair-housed [for anticipatory nausea and light-dark emergence studies] in home cages made of opaque white plastic (48× 26×20 cm), containing bed-o-cob bedding from Harlan Laboratories, Inc. (Mississauga, Ontario), a brown paper towel, and Crinkl'Nest™ from The Andersons, Inc. (Maumee, Ohio). Additionally, in the home cage, rats were provided with a soft white paper container that was 14 cm long and 12 cm in diameter. All rats were subjected to an ambient temperature of 21° C. and a 12/12 h light-dark schedule (lights off at 07:00 h) and maintained on food (Highland Rat Chow [8640]) and water ad libitum. For the acute and anticipatory nausea studies, their body weights ranged from 263 to 329 g on the day of conditioning. For the light-dark emergence studies, their body weights ranged from 320 to 387 g on the day of test.

Apparatus.

For the studies of acute nausea (in vivo experiment 1), rats were placed in taste reactivity (Grill and Norgren, 1978) chambers with their cannula attached to an infusion pump (Model KDS100, KD Scientific, Holliston, Mass., USA) for fluid delivery. The taste reactivity chambers were made of clear Plexiglas (22.5×26×20 cm) that sat on a table with a clear glass top. A mirror beneath the chamber at a 45° angle facilitated viewing of the ventral surface of the rat to observe orofacial responses. The conditioning chamber was in a dark room next to a 25 W light source. A video camera (Sony DCR-HC48, Henry's Cameras, Waterloo, ON, Canada) fire-wired into a computer was focused on the mirror and used to record each rat's orofacial reactions during the 2 min taste reactivity test. The video tapes were later scored using 'The Observer' (Noldus Information Technology Inc., Leesburg, Va., USA) software.

For in vivo experiment 2, contextually elicited conditioned gaping (a model of anticipatory nausea) was measured using a distinctive conditioning chamber made of opaque black Plexiglass (22.5×26×20 cm) with an opaque lid that sat on a table with a clear glass top. A mirror beneath the chamber at a 45° angle facilitated viewing of the ventral surface of the rat to observe orofacial responses. The conditioning chamber was in a dark room next to a 25 W light source. A video camera that was fire-wired into a computer was focused on the mirror to record each rat's orofacial reactions during the 5 min test trial. The video tapes were later scored using 'The Observer' software. To assess activity, an activity chamber made of white Plexiglas (60×25×25 cm) was used, illuminated by a red light found in a different room that the contextual chamber was used to create a different context from the AN chamber. The activity of each rat was captured by video camera and sent to the Ethovision software program (Noldus, Inc., NL) to measure distance (cm) travelled.

For the in vivo experiment 3, anxiolytic-like responding was evaluated using the light-dark emergence apparatus, which consisted of an opaque white plastic rectangular box that was divided into two compartments: a small (25 cm wide×20.5 cm long×20.5 cm high) enclosed dark box built of opaque black plastic with a door (8 cm wide×10 cm high) leading to a larger (39.5 cm long×25 cm wide) open lit box. The open lit box was illuminated by one lamp (with a 60 W bulb, 180 lux in the light chamber) positioned 115 cm above the center of the lit box. A video camera was mounted over the top of the light-dark box, and the video tapes were analyzed by the Ethovision software (Noldus Information Technology, Leesburg, Va., USA) for the duration of time spent in the light box for the 5 min test. For the foot shock (FS) session, the rats were placed in sound attenuating MED Associates fear conditioning chambers (St. Albans, Vt., USA). The 6 min FS session consisted of six 0.8 mA foot shocks delivered 1 min apart. Each 0.5 s shock was preceded by a 30 s auditory tone (90 Db, 5000 Hz) as described by Bluett et al. (2014).

In Vivo Procedures

In Vivo Experiment 1: Dose-Related Effects of CBDA and HU-580 on Acute Nausea and $5\text{-HT}_{1A}$ Receptor Mediation of HU-580 Effects.

All rats were surgically implanted with an intraoral cannula according the procedures described by Limebeer et al. (2010). On the day of surgery, the rats were injected with an antibiotic (Derapin: 00 mg·kg$^{-1}$ s.c.; Pfizer Animal Health, Pfizer Canada Inc, Kirkland, Quebec, Canada) 30 min prior to being anaesthetized with isoflurane (4-5% induction, 1.5% maintenance in $O_2$). Surgical plane anesthesia, as indicated by absence of the hind limb withdrawal reflex and defined by the Canadian Council of Animal Care, was induced before any surgery began, and was adjusted as necessary. Once sufficient anesthesia had been induced, a 2 cm$^2$ section of skin was shaved at the back of the neck at the level of the scapula. The skin was prepared by cleaning with soap (Bactistat; Ecolab, St. Paul, Minn., USA) and wiping with 70% isopropyl alcohol followed by 7% Betadine solution (Purdue Products L.P., Stamford, Conn., USA). Each rat was then administered a 5 mg·kg$^{-1}$ injection (i.p.) of the anti-inflammatory/analgesic drug carprofen (Rimadyl; Pfizer Canada Inc., Kirkland, Quebec, Canada). A thin-walled 15-gauge stainless steel needle was inserted into the shaved area on the neck, directed subcutaneously around the ear and brought out behind the first molar inside the mouth. A 10 cm length of Intra Medic PE90 tubing (Clay Adams Brand; Becton Dickinson and Co., Sparks, Md., USA) with an inner diameter of 0.86 mm and an outer diameter of 1.27 mm was then inserted through the needle after which the needle was removed. Betadine (10%) was applied to the puncture site and three elastic discs (2 cm$^2$) were placed over the exposed end of the tubing and drawn to the skin at the back of the neck for the purpose of stabilizing the cannula. The cannula was held secure in the oral cavity by a 6 mm disc of polypropylene mesh (297 micron; Small Parts Inc., Miramar, Fla., USA) secured behind the heat flanged intraoral opening. The rats were then returned to their home cage and monitored daily for 3 days. For 3 days following surgery the rats were weighed and their cannulae were flushed with an antiseptic mouth wash. During this time, the rats were also monitored for activity, vocalization, dehydration, rigidity, and presence of porphyrin staining around the eyes. On the first post-surgical day, the rats were also given an analgesic/anti-inflammatory injection of Rimadyl (5 mg·kg$^{-1}$ i.p.).

Following post-surgical monitoring, the rats received an adaptation trial in which they were placed in the taste reactivity chamber with each rat's cannula attached to the infusion pump. During adaptation, water was infused into their intraoral cannulae for 2 min at a rate of 1 mL·min$^{-1}$. On the day following the adaptation trial, the rats received a conditioning trial in which they were administered a pretreatment injection of vehicle (VEH) (n=8), CBDA (0.01, 0.1, 1 µg·kg$^{-1}$; n=8 per group) or HU-580 (0.01, 0.1, 1 µg·kg$^{-1}$; n=8 per group). Forty-five minutes after the pretreatment injection, the rats were individually placed in the chamber and infused, p.o., with 0.1% saccharin solution for 2 min at the rate of 1 mL·min$^{-1}$. Immediately after the saccharin infusion, all rats were injected with 20 mL·kg$^{-1}$ of 0.15 M LiCl and returned to their home cage. Seventy-two hours later, rats were tested drug-free. Rats were again infused p.o. with 0.1% saccharin solution for 2 min at the rate of 1 mL·min$^{-1}$ while the orofacial responses were video recorded from a mirror at a 450 angle beneath the chambers. Rats were then returned to their home cages. Two additional groups were added to determine the mechanism of action. These rats were injected with WAY100635 (0.1 mg·kg$^{-1}$) 15 min prior to an injection of either vehicle (n=8) or 0.1 µg·kg$^{-1}$ HU-580 (n=6). The video tapes were later scored by an observer blind to the experimental conditions using 'The Observer' for the behaviors of gaping (large openings of the mouth and jaw, with lower incisors exposed).

In Vivo Experiment 2: Effect of CBDA and HU-580 on Anticipatory Nausea and $5\text{-HT}_{1A}$ Receptor Mediation of HU-580 Effects.

To compare the potential of HU-580 and CBDA to reduce anticipatory nausea, the contextually elicited conditioned gaping paradigm was used (e.g. Limebeer et al., 2010; Rock et al., 2014). Rats underwent four conditioning trials during which the distinctive context was paired with 127 mg·kg$^{-1}$ LiCl. On each trial, rats were injected with LiCl and then immediately placed in the conditioning chamber for 30 min. This procedure was repeated four times with a 48 h interval between conditioning trials. For the test trial, rats were randomly assigned to one of five treatment groups (n=6 per group): VEH, 0.1 µg·kg$^{-1}$ CBDA, 0.1 µg·kg$^{-1}$ HU-580, 0.01 µg·kg$^{-1}$ CBDA, 0.01 g·kg$^{-1}$ HU-580. Pretreatments were injected 45 min before the rats were given an saline injection (20 mL·kg$^{-1}$ i.p.) and individually placed in the conditioning (contextual) chamber for 5 min, and orofacial responses were video recorded. To investigate the mechanism of action of HU-580, two additional groups of rats were administered 0.1 mg·kg$^{-1}$ WAY-VEH (n=8), 0.1 mg·kg$^{-1}$ WAY-0.1 µg·kg$^{-1}$ HU-580 (n=8). VEH or WAY100635 were administered 15 min before HU-308 or VEH. The video tapes from the test trial were scored by an observer blind to the experimental conditions using 'The Observer' for the behaviors of gaping (large openings of the mouth and jaw, with lower incisors exposed). Immediately following the test trial, rats were put in the activity chamber (white Plexiglas, 60×25×25 cm, illuminated by a red light) for 15 min, and locomotor activity was captured by a video camera and sent to a computer using EthoVision software (Noldus, Inc, NL) to measure distance (cm) travelled.

In Vivo Experiment 3: Effect of CBDA and HU-580 on Anxiety-Like Responding and $5\text{-HT}_{1A}$ Receptor Mediation of HU-580 Effects.

The effect of CBDA and HU-580 on anxiety-like responding was evaluated using the light-dark box emergence test following either foot shock stress or no foot shock (No FS) stress. Bluett et al. (2014) have demonstrated that anxiety-like responding in this test is greatly enhanced 24 h following foot shock stress. Also, Rock et al. (2017) have shown that CBDA (at doses as low as 0.1 µg·kg$^{-1}$ i.p.) prevents the enhanced anxiety-like responding following foot shock stress, by a 5-HT$_{1A}$-dependent mechanism of action. Therefore, the relative effectiveness of an even lower dose (0.01 µg·kg$^{-1}$, i.p) of CBDA and HU-508 was compared. Since it was found that HU-580 was anxiolytic at this low dose, it was subsequently evaluated the ability of the 5HT$_{1A}$ receptor antagonist, WAY100635, to reverse the suppression of anxiety-like responding by HU-580.

All rats were acclimatized to the facility for 13 days prior to experimental manipulations, with weighing and handling occurring for eight of these days. After this acclimatization, the rats received a single FS stress session or No FS stress session 24 h before the light-dark emergence test (Bluett et al., 2014). For the FS group, the rats were placed in sound-attenuating MED Associates fear conditioning chambers (St. Albans, Vt., USA). The 6 min FS session consisted of six 0.8 mA FSs delivered 1 min apart. Each 0.5 s shock was preceded by a 30 s auditory tone (90 Db, 5000 Hz) as described by Bluett et al. (2014). The No FS stress group remained in their home cage during this session.

Twenty-four hours later, the rats were subjected to the light-dark emergence test. Rats in the FS group and the No FS group were pretreated with VEH, 0.01 µg·kg$^{-1}$ CBDA or 0.01 µg·kg$^{-1}$ HU-580. Forty-five minutes later, they were placed in the dark chamber of the light-dark box, and their movement was tracked for a 5 min test. To investigate the possibility that the effect of HU-580 was 5-HT$_{1A}$ receptor-mediated, additional groups were injected with WAY100635, 15 min prior to VEH or 0.01 g·kg$^{-1}$ HU-580. The number of seconds spent in the light box was measured. Groups were as follows: No FS-VEH (n=9), FS-VEH (n=12), No FS-0.01 µg·kg$^{-1}$ CBDA (n=8), FS-0.01 µg·kg$^{-1}$ CBDA (n=8), No FS-0.01 HU-580 (n=8), FS-0.01 HU-580 (n=8), No FS-0.1 µg·kg$^{-1}$ WAY-VEH (n=8), FS-0.1 µg·kg$^{-1}$ WAY-VEH (n=7), No FS-0.1 µg·kg$^{-1}$ WAY-0.01 µg·kg$^{-1}$ HU580 (n=8), FS-0.1 µg·kg$^{-1}$ WAY-0.01 µg·kg$^{-1}$ HU-580 (n=8).

In Vitro and In Vivo Data Analysis

Net agonist-stimulated [$^{35}$S]-GTPγS binding values were calculated by subtracting basal binding values (obtained in the absence of agonist) from agonist-stimulated values (obtained in the presence of agonist) (Cascio et al., 2010). Values are expressed as means and variability as SEM or as 95% confidence limits. Mean EC$_{50}$ and mean maximal effect (E$_{max}$) values, and SEM or 95% confidence limits of these values, have been calculated by nonlinear regression analysis using the equation for a sigmoid concentration-response curve (GraphPad Prism). P values<0.05 were considered significant. The data and statistical analysis comply with the recommendations on experimental design and analysis in pharmacology (Curtis et al., 2015).

For analysis of data from the acute nausea experiment (In vivo experiment 1), a single factor ANOVA was conducted for the mean number of gapes in the 2 min test, and subsequent pairwise comparisons were assessed with least significant difference (LSD) post hoc tests. For analysis of data from the anticipatory nausea (AN) experiment (In vivo experiment 2), a single factor ANOVA was conducted for the number of gapes in the 5 min AN test and for the total distance travelled in the activity test, and subsequent pairwise comparisons were assessed with LSD post hoc tests. For analysis of data from the anxiety-like responding experiment (In vivo experiment 3), the amount of time spent in the light box during the light-dark emergence test was entered into a 2×5 between factors ANOVA with the factors of FS stress/No FS stress and each pretreatment and µg·kg$^{-1}$ i.p. dose condition (VEH, 0.01 µg·kg$^{-1}$ CBDA, 0.01 µg·kg$^{-1}$ HU-580, WAY-VEH or WAY-HU-580). Subsequent independent t-tests were conducted to explore the interaction. Significance levels were set at P<0.05.

Drugs and materials used in vitro. 8-OH-DPAT and WAY100635 were supplied by Bio-Techne (Abingdon, UK). [$^{35}$S]-GTPγS (1250 Ci mmol$^{-1}$) was purchased from PerkinElmer Life Sciences, Inc. (Boston, Mass., USA), and GTPγS, GDP and DMSO from Sigma-Aldrich UK. CBDA and its methyl ester (HU-580) were provided by Raphael Mechoulam.

Drugs Used In Vivo.

Lithium chloride (LiCl; Sigma Aldrich) was prepared in a 0.15 M solution with sterile water and was administered i.p. at a volume of 20 mL·kg$^{-1}$ (127.2 mg·kg$^{-1}$ dose). CBDA and its methyl ester (HU-580), both provided by Raphael Mechoulam, were dissolved in a glass graduated tube in 1 mL ethanol with 1 mL Tween80 (Sigma) added to the solution, and the ethanol was evaporated off with a nitrogen stream, after which 9 mL of saline was added (final Tween80:saline ratio=1:9). CBDA or HU-580 were administered to rats i.p. at a dose of 0.01, 0.1 or 1.0 µg·kg$^{-1}$, in a volume of 1 mL·kg$^{-1}$, using a stock solution containing one or other of these compounds at a concentration of 0.01, 0.1 or 1.0 µg·mL$^{-1}$ respectively. WAY100635 (Sigma, St Louis, Mo., USA) was dissolved in saline at a concentration of 0.1 mg·mL$^{-1}$ and administered to rats i.p. at a dose of 0.1 mg·kg$^{-1}$ (1 mL·kg$^{-1}$).

Results

CBDA and HU-580 Enhance the Ability of a 5-HT$_{1A}$ Receptor Agonist to Stimulate [$^{35}$S] GTPγS Binding to Human 5-HT$_{1A}$ Receptors In Vitro As found previously in [$^{35}$S]GTPγS binding experiments performed with rat brainstem membranes (Bolognini et al., 2013), CBDA enhanced the stimulation of [$^{35}$S]-GTPγS binding induced by the selective 5-HT$_{1A}$ receptor agonist, 8-OH-DPAT, to membranes obtained from CHO cells stably transfected with human 5-HT$_{1A}$ receptors (FIG. 1A-1E and Table 1). Concentrations of CBDA in the sub-micromolar range, producing significant increases in the mean E$_{max}$ of 8-OH-DPAT at 0.1, 1.0 and 10 nM, but not at 0.01 or 100 nM. None of these increases in mean E$_{max}$ was accompanied by any significant change in the mean EC$_{50}$ of 8-OH-DPAT (P>0.05; Table 1). The methyl ester of CBDA, HU-580, was even more potent than CBDA at enhancing 8-OH-DPAT-induced stimulation of [$^{35}$S]-GTPγS binding to human 5-HT$_{1A}$ receptor-expressing CHO cell membranes (FIG. 2A-2F and Table 2). Thus, it produced a significant increase in the mean E$_{max}$ of 8-OH-DPAT not only at 0.1, 1.0 and 10 nM (like CBDA) but also at 0.01 nM (unlike CBDA). HU-580 did not increase the mean E$_{max}$ of 8-OH-DPAT either at 100 nM (like CBDA) or at 0.001 nM and did not significantly affect the mean EC$_{50}$ of 8-OH-DPAT at any of the concentrations investigated (Table 2). When administered by itself, at concentrations of 0.01, 0.1, 1, 10 or 100 nM, HU-580 did not behave as a 5-HT$_{1A}$ receptor agonist or inverse agonist as indicated by the lack of a detectable effect of any of these concentrations on [$^{35}$S]-GTPγS binding to membranes obtained from human 5-HT$_{1A}$ receptor-transfected CHO cells (n=6; data not shown).

TABLE 1

Effects of various concentrations of CBDA on the mean $EC_{50}$ and $E_{max}$ values of 8-OH-DPAT for its stimulation of [$^{35}$S]GTPγS binding to membranes obtained from CHO cells stably transfected with human $5\text{-}HT_{1A}$ receptors (See also FIGS. 1A-1E)

| Pretreatment | Mean $EC_{50}$ (nM) | 95% confidence limits (nM) | Mean $E_{max}$ (%) | 95% confidence limits (%) | n |
|---|---|---|---|---|---|
| Vehicle | 17.48 | 10.14 & 30.12 | 97.69 | 88.57 & 106.8 | 6 |
| 0.01 nM CBDA (FIG. 1A) | 22.66 | 10.32 & 49.46 | 95.64 | 83.23 & 108.1 | 6 |
| Vehicle | 10.77 | 5.74 & 20.21 | 98.67 | 88.26 & 109.1 | 6 |
| 0.1 nM CBDA (FIG. 1B) | 11.19 | 8.18 & 15.29 | 115.3* | 109.6 & 120.9 | 6 |
| Vehicle | 15.52 | 7.51 & 32.08 | 96.56 | 84.51 & 108.6 | 6 |
| 1.0 nM CBDA (FIG. 1C) | 72.81 | 31.86 & 166.4 | 167.1* | 138.3 & 195.9 | 6 |
| Vehicle | 16.77 | 8.58 & 32.80 | 101.7 | 89.55 & 113.9 | 6 |
| 10 nM CBDA (FIG. 1D) | 57.44 | 23.55 & 140.1 | 143.9* | 118.4 & 169.4 | 6 |
| Vehicle | 20.00 | 11.46 & 34.88 | 108.6 | 98.03 & 119.1 | 6 |
| 100 nM CBDA (FIG. 1E) | 22.86 | 10.73 & 48.70 | 109.0 | 96.14 & 121.9 | 6 |

Each asterisk indicates a significant difference (*P<0.05) between a mean $E_{max}$ value of 8-OH-DPAT determined in the presence of a particular concentration of CBDA, and the mean $E_{max}$ value of 8-OH-DPAT displayed in the previous row, that was determined in the same experiment in the presence of vehicle (DMSO) instead of CBDA. Significant differences are indicated by non-overlapping 95% confidence limits.

TABLE 2

Effects of various concentrations of HU-580 on the mean EC50 and $E_{max}$ values of 8-OH-DPAT for its stimulation of [$^{35}$S]GTPγS binding to membranes obtained from CHO cells stably transfected with human $5\text{-}HT_{1A}$ receptors (see also FIGS. 2A-2F)

| Pretreatment | Mean $EC_{50}$ (nM) | 95% confidence limits (nM) | Mean $E_{max}$ (%) | 95% confidence limits (%) | n |
|---|---|---|---|---|---|
| Vehicle | 18.05 | 10.73 & 30.38 | 102.4 | 93.21 & 111.7 | 6 |
| 0.001 nM HU-580 (FIG. 2A) | 14.44 | 9.37 & 22.25 | 99.80 | 98.33 & 106.3 | 6 |
| Vehicle | 15.49 | 7.84 & 30.59 | 96.25 | 85.34 & 107.2 | 6 |
| 0.001 nM HU-580 (FIG. 2B) | 34.15 | 18.58 & 62.77 | 126.9* | 113.5 & 140.3 | 6 |
| Vehicle | 18.69 | 9.74 & 35.83 | 97.62 | 86.22 & 109.0 | 6 |
| 0.1 nM HU-580 (FIG. 2C) | 12.94 | 6.88 & 24.34 | 125.3* | 113.0 & 137.6 | 6 |
| Vehicle | 19.75 | 11.44 & 34.12 | 108.4 | 98.0 & 118.7 | 6 |
| 1.0 nM HU-580 (FIG. 2D) | 48.22 | 31.31 & 74.26 | 140.5* | 128.7 & 152.4 | 6 |
| Vehicle | 14.58 | 6.83 & 31.15 | 99.36 | 86.58 & 112.1 | 6 |
| 10 nM HU-580 (FIG. 2E) | 23.94 | 8.82 & 64.97 | 138.8* | 115.7 & 161.9 | 6 |
| Vehicle | 19.89 | 11.78 & 33.58 | 101.6 | 92.04 & 111.1 | 6 |
| 100 nM HU-580 (FIG. 2F) | 8.49 | 1.87 & 38.59 | 91.96 | 71.6 & 112.3 | 6 |

Each asterisk indicates a significant difference (*P<0.05) between a mean $E_{max}$ value of 8-OH-DPAT determined in the presence of a particular concentration of HU-580, and the mean $E_{max}$ value of 8-OH-DPAT displayed in the previous row, that was determined in the same experiment in the presence of vehicle (DMSO) instead of HU-580. Significant differences are indicated by non-overlapping 95% confidence limits.

Figure 3:
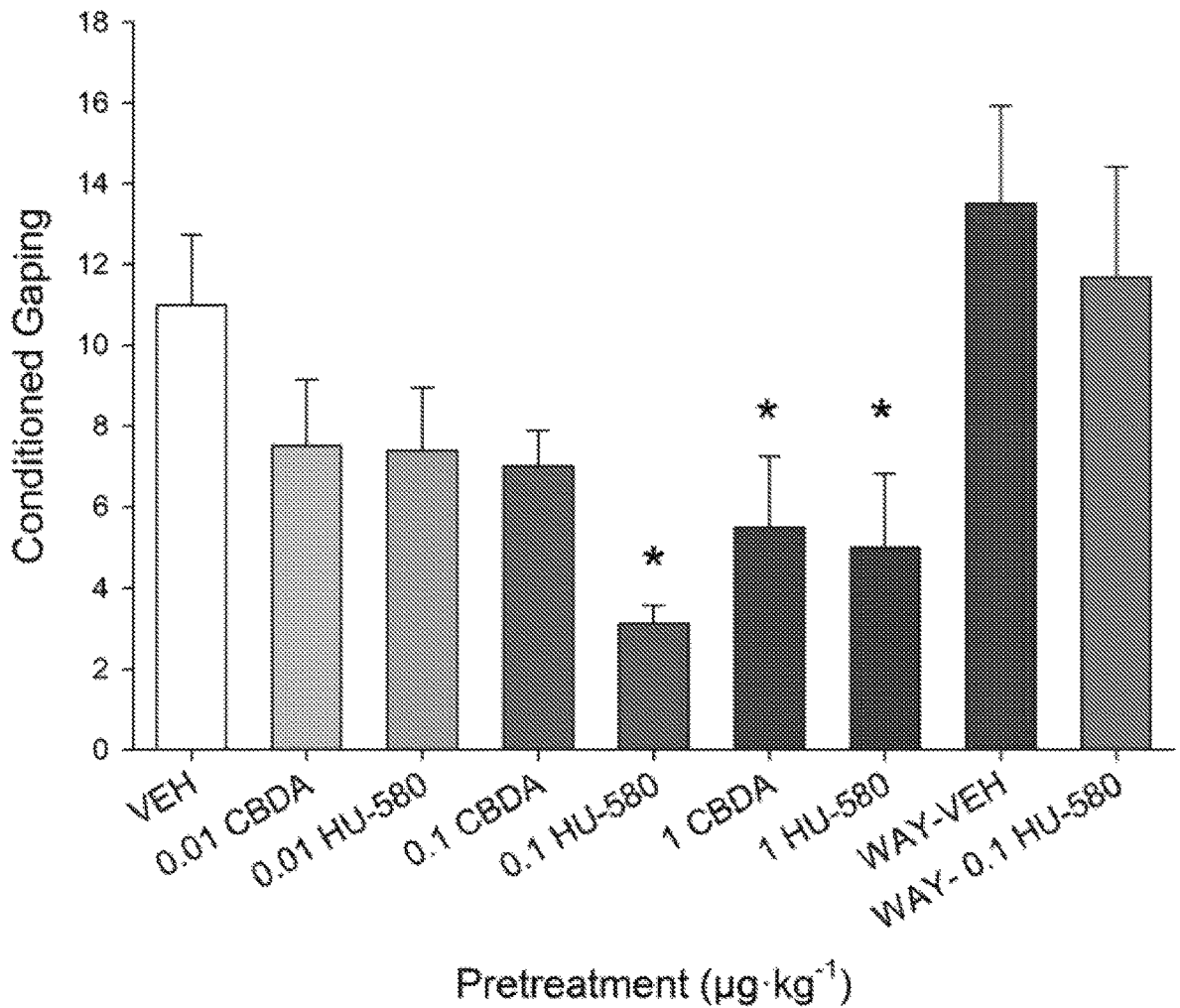
FIG. 3 shows the mean number of conditioned gapes elicited by a LiCl-paired saccharin solution among the rats pretreated with various doses of CBDA (n=8 per group) or HU-580 (n=8 per group) or just with vehicle (VEH; n=8). Additional groups were administered a pretreatment of WAY100635 (0.1 mg·kg-1) 15 min prior to 0.1 mg·kg-1 HU-580 (n=6) or VEH (n=8). Results are presented as mean±SEM and *P<0.05, depicts mean responses to CBDA or HU-580, which differed significantly from mean responses to VEH.

In Vivo Experiment 1: Dose-Related Effects of CBDA and HU-580 on Acute Nausea and $5\text{-}HT_{1A}$ Receptor Mediation of HU-580 Effects At a dose of 0.1 µg·kg$^{-1}$, but not at 0.01 or 1 µg·kg$^{-1}$, HU-580 was more effective than CBDA in reducing acute nausea as assessed by the rat gaping model. HU-580's suppressive effect on acute nausea (0.1 µg·kg$^{-1}$) was blocked by WAY100635. A single factor ANOVA revealed a significant group effect $F(8, 61)=3.9$; $P<0.05$. FIG. 3 presents the mean number of gapes displayed by the various pretreatment groups. Subsequent LSD post hoc comparison tests revealed that both compounds reduced LiCl-induced gaping responses relative to vehicle at a dose of 1 µg·kg$^{-1}$ ($P<0.05$), replicating our previous findings (Limebeer et al., 2010; Rock and Parker, 2013). However, at the even lower dose of 0.1-µg·kg$^{-1}$, that is, subthreshold for a CBDA-induced reduction of nausea-like behavior, HU-580 reduced LiCl-induced conditioned gaping behavior relative to vehicle (P<0.05). Rats pretreated with HU-580 (0.1 μg·kg$^{-1}$) also gaped significantly less than group WAY-0.1 μg·kg$^{-1}$ HU-580 (P<0.05), indicating a 5-HT$_{1A}$ receptor-mediated effect.

Figure 4A:
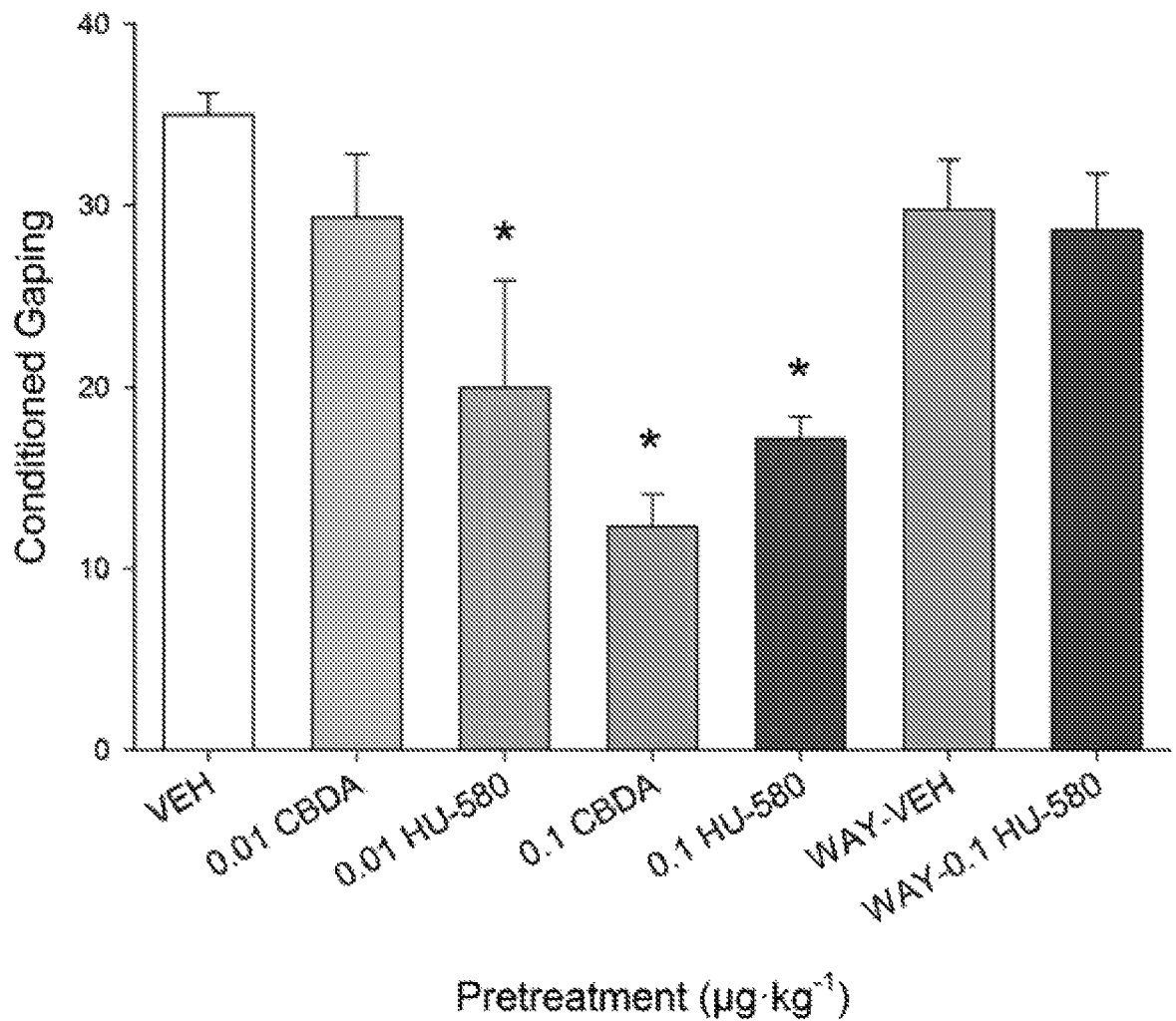
FIG. 4A shows the effect of CBDA or HU-580 (0.01, 0.1 μg·kg$^{-1}$) or vehicle (VEH) administered i.p. 45 min prior to the anticipatory nausea test (n=6 per group). Additional groups were administered a pretreatment of WAY100635 (0.1 mg·kg$^{-1}$) 15 min prior to 0.1 mg·kg$^{-1}$ HU-580 (n=8) or VEH (n=8). The mean number of conditioned gaping responses was measured during the anticipatory nausea test trial. Each bar represents the mean±SEM. *P<0.05, significant difference from the VEH-treated control animals.
Figure 4B:
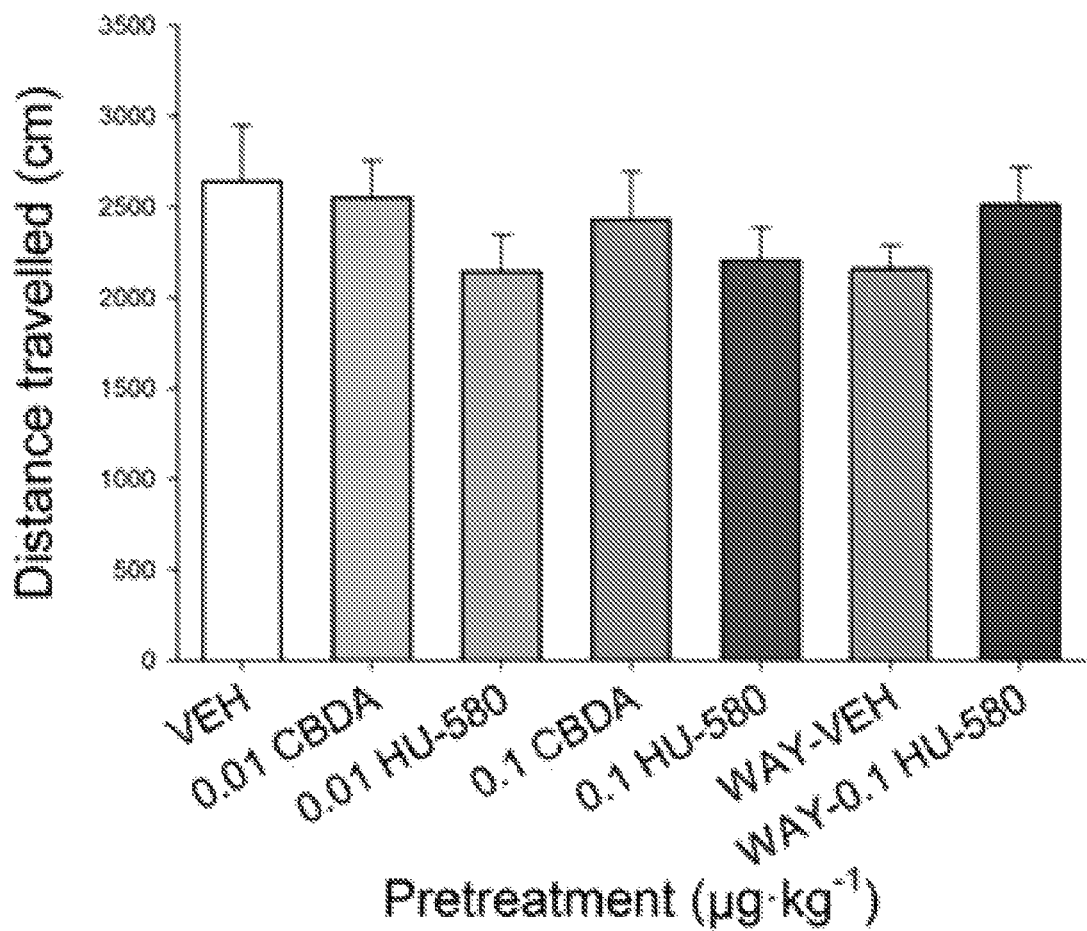
FIG. 4B shows the mean distance (cm) travelled was measured in an activity test performed after the anticipatory nausea test. Each bar represents the mean±SEM.

In Vivo Experiment 2: Effect of CBDA and HU-580 on Anticipatory Nausea and 5-HT$_{1A}$ Receptor Mediation of HU-580 Effects At an extremely low dose of 0.01 μg·kg$^{-1}$, but not at 0.1 μg·kg$^{-1}$, HU-580 was more effective than CBDA in reducing anticipatory nausea as assessed by the contextually elicited conditioned gaping model. The suppressive effect of HU-580 (0.1 μg·kg$^{-1}$) was blocked by pretreatment with WAY100635. A single factor ANOVA revealed a significant group effect F(6, 39)=8.7; P<0.05. FIG. 4A presents the mean number of gapes displayed. Subsequent LSD post hoc comparisons revealed that compared to VEH controls, at a dose of 0.1 μg·kg$^{-1}$, both CBDA and HU-580 reduced conditioned gaping (P values<0.05); however, the groups did differ at a dose of 0.01 μg·kg$^{-1}$, with group HU-580 gaping significantly less than VEH controls (P<0.05) and group 0.01 CBDA (P=0.05). Rats pretreated with HU-580 (0.1 μg·kg$^{-1}$) also gaped significantly less than group WAY-0.1 μg·kg$^{-1}$ HU-580 (P<0.05), indicating a 5-HT$_{1A}$ receptor-mediated effect. A single factor ANOVA for the locomotor activity test (FIG. 4B) revealed no significant effect on distance moved, F(6, 39)=0.9, P>0.05.

In Vivo Experiment 3: Anxiolytic Effects of CBDA and HU-580

Figure 5:
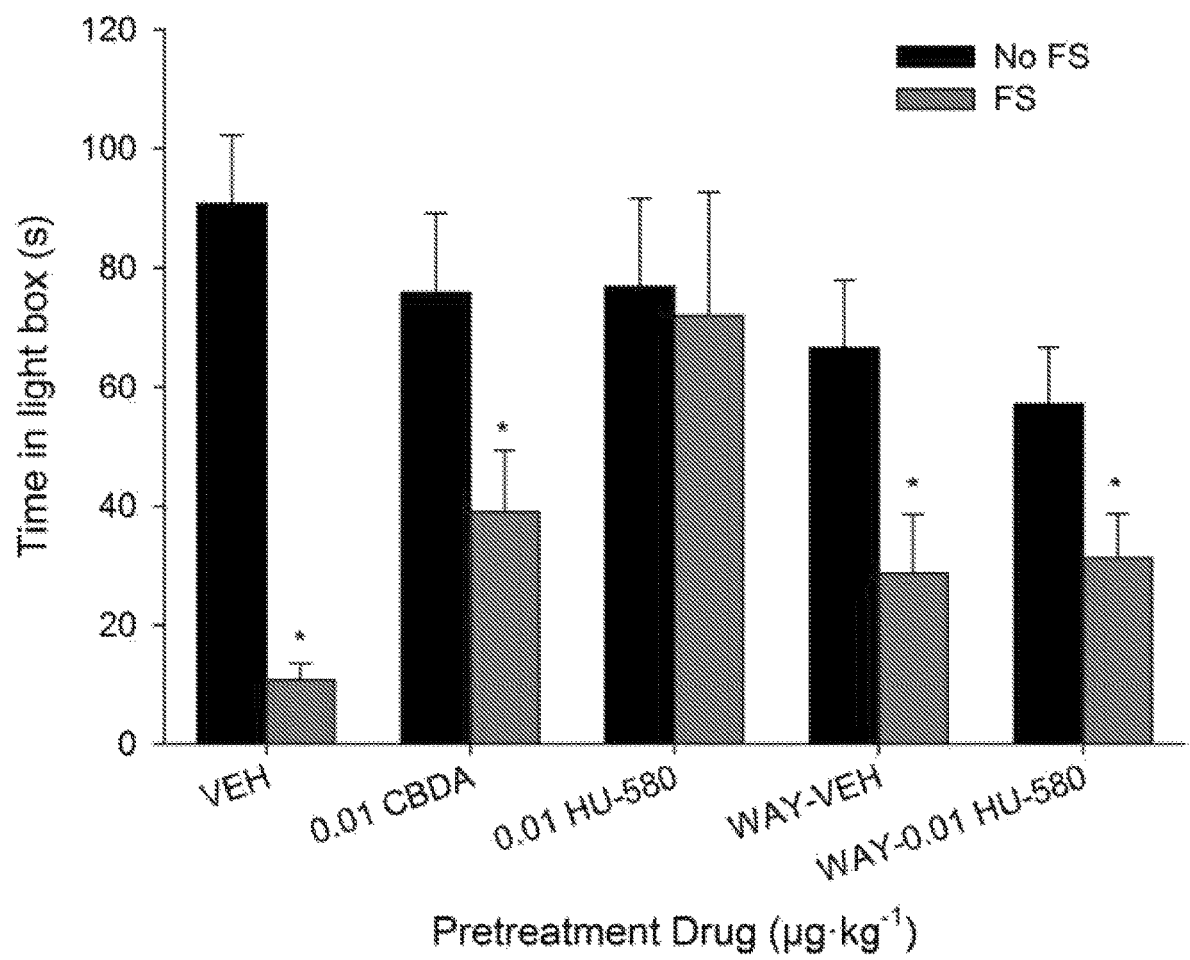
FIG. 5 shows the mean time spent by rats in the light box, 24 h following exposure to no foot shocks (No-FS) or to FSs. All rats were injected i.p. with vehicle (VEH; n=9 or 12), 0.01 μg·kg$^{-1}$, CBDA (n=8) or 0.01 μg·kg$^{-1}$ HU-580 (n=8), 45 min prior to a 5 min light-dark box emergence test. Additional groups were injected with 0.1 mg·kg$^{-1}$ WAY100635 15 min prior to VEH (n=7 or 8) or 0.01 μg·kg$^{-1}$ HU-580 (n=8). Each bar represents the mean±SEM. *P<0.05, indicates a significant difference between FS and No FS stress groups.

FIG. 5 presents the mean number of seconds spent by rats in the light box for each of the various pretreatment groups that received FS or No FS 24 h prior the light-dark test. As can be seen, FS stress greatly enhanced the anxiety-like responding of decreased time spent in the light box. At a low dose of 0.01 μg·kg$^{-1}$, HU-580, but not CBDA, reversed the effect of FS on the anxiety-like responding of decreased time spent in the light box. The 2×5 ANOVA for the number of seconds spent in the light box revealed a significant main effect of FS stress, F(1, 84)=25.6; P<0.05, and a FS stress× pretreatment interaction, F(4, 84)=3.2; P, 0.05). To analyze the interaction, subsequent independent t-tests revealed that rats pretreated with VEH (P<0.05), 0.01 μg·kg$^{-1}$ CBDA (P<0.05), WAY-VEH (P<0.05) or WAY-0.01 μg·kg$^{-1}$ HU-580 (P=0.05) spent less time in the light box following FS stress than following No FS stress, but rats pretreated with 0.01 μg·kg$^{-1}$ HU-580 did not display this anxiogenic-like response. Furthermore, subsequent single factor ANOVAs of the time spent in the light box revealed a significant pretreatment effect among the FS groups, F(4, 38)=4.6; P<0.05, but not among the No FS groups. Among the FS groups subsequent Bonferroni tests revealed that only group 0.01 μg·kg$^{-1}$ HU-580 spent significantly more time in the light box than group VEH (P<0.05).

DISCUSSION

The results obtained confirmed that CBDA displays significant potency both at producing an apparent enhancement of the activation of 5HT$_{1A}$ receptors, by the direct 5-HT$_{1A}$ receptor agonist, 8-OH-DPAT, in vitro, and at producing a 5-HT$_{1A}$ receptor-mediated reduction of both acute and anticipatory nausea in rats, in vivo.

The new in vitro data shows, first, that CBDA can enhance the activation not only of rat brain stem 5-HT$_{1A}$ receptors (Bolognini et al., 2013), but also of human 5-HT$_{1A}$ receptors and, second, that at both rat brain stem and human 5-HT$_{1A}$ receptors, CBDA induces such enhancement with a bell-shaped concentration-response curve in the sub-micromolar range. The in vitro data described herein also reveals an important similarity between the pharmacological effects of CBDA and its methyl ester, HU-580. More specifically, these data have provided convincing evidence that HU-580 shares the ability of CBDA to produce an apparent enhancement of the activation of human 5-HT$_{1A}$ receptors by 8-OH-DPAT in the [$^{35}$S]-GTPγS binding assay. Importantly, HU-580 produced such enhancement both with greater potency and with an even broader bell-shaped concentration-response curve than CBDA. Thus, significant enhancement was induced by HU-580 at concentrations of 0.01 to 10 nM (Table 2) and by CBDA at concentrations of 0.1 to 10 nM (Table 1). Whereas, at concentrations of 1, 10 and 100 nM, HU-580 produced slightly less enhancement of 8-OH-DPAT-induced 5-HT$_{1A}$ receptor activation than CBDA, HU-580 produced slightly greater enhancement of this activation than CBDA, at concentrations of 0.01 and 0.1 nM (Tables 1 and 2).

It is noteworthy that none of the concentrations of CBDA and HU-580 that significantly increased E$_{max}$ values of 8-OH-DPAT for its stimulation of [$^{35}$S]-GTPγS binding to 5-HT$_{1A}$ receptors produced any significant change in the EC$_{50}$ of 8-OH-DPAT (Tables 1 and 2). This finding shows that CBDA and HU-580 may have been acting as positive allosteric modulators of the activation of these receptors by 8-0H-DPAT, there being evidence that some positive allosteric modulators do indeed increase the E$_{max}$ values but not the potencies of agonists at certain receptors (Christopoulos et al., 2014). There is a possibility that CBDA and HU-580 target an allosteric site on the 5-HT$_{1A}$ receptor, as positive allosteric modulators. It is also noteworthy that the positive in vitro data for CBDA and HU-580 that was obtained herein all came from experiments performed with CHO cells transfected with human 5-HT$_{1A}$ receptors.

The in vivo data reveals similarities between the pharmacological effects of HU-580 and CBDA. Thus, these data show that the ability of CBDA to reduce acute and anticipatory nausea in rats extends to HU-580. Importantly, as also found in our in vitro experiments, HU-580 displayed even greater potency than CBDA. More specifically, effective suppression of acute nausea-induced conditioned gaping was induced by HU-580 at a dose as low as 0.1 μg·kg$^{-1}$ i.p., whereas the lowest effective dose of CBDA for the production of such suppression was 1 μg·kg$^{-1}$ i.p. (FIG. 3). Indeed, it was found that at a dose as low as 0.01 μg·kg$^{-1}$ i.p., HU-580, but not CBDA, suppressed contextually elicited conditioned gaping. It was also shown that suppression of LiCl-induced gaping and contextually elicited conditioned gaping by HU-580 can be completely prevented by the 5-HT$_{1A}$ receptor-selective antagonist, WAY100635. Finally, although CBDA has recently been found to reduce FS enhancement of anxiogenic-like behavior in the light-dark box emergence test at doses of 0.1, 1 and 100 μg·kg$^{-1}$ i.p. (Rock et al., 2017), it was found herein that it did not share the ability of HU-580 to reduce FS enhancement of anxiogenic-like behavior in the light-dark emergence test at the lower dose of 0.01 μg·kg$^{-1}$ i.p., suggesting that HU-580 may be even more potent than CBDA in reducing stress-induced anxiety. Furthermore, it was also shown that HU-580 has the ability to reduce FS enhancement of anxiogenic-like behavior is 5-HT$_{1A}$ receptor-mediated. The results show that HU-580 is both more stable than CBDA, and more potent than CBDA (acute and anticipatory nausea).

Ideally, drugs used as medicines should, when stored, display stability over a reasonable period of time. Hence, since stored CBDA undergoes significant decomposition, even at 4° C., a major aim of this project was to develop a compound that produces no less potency than CBDA in the assays described in this paper but displays much greater stability over a reasonable length of time when stored at this temperature. It is noteworthy, therefore, that the inventors have found that HU-580 is, indeed, more stable than CBDA when stored at 4° C. for 21 days. In addition, the finding showing that HU-580 is more potent than CBDA both in vitro and in vivo supports the hypothesis that the pharmacological effects produced by HU-580 in our experiments did not depend on its decomposition or metabolism to CBDA.

In conclusion, the evidence shows that HU-580, displays greater potency than CBDA at suppressing signs both of acute and anticipatory nausea, and of stress-induced anxiety in rats, and that it produces these effects in a $5HT_1$ receptor-dependent manner.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

REFERENCES

Alexander S P H, Christopoulos A, Davenport A P, Kelly E, Marrion N V, Peters J A et al. (2017). THE CONCISE GUIDE TO PHARMACOLOGY 2017/18: G protein-coupled receptors. Br J Pharmacol 174: S 17-S 129.

Bluett R J, Gamble-George J C, Hermanson D J, Hartley N D, Marnett L J, Patel S (2014). Central anandamide deficiency predicts stress-induced anxiety: behavioral reversal through endocannabinoid augmentation. Transl Psychiatry 4: e408. https://doi.org/10.1038/tp.2014.53.

Bolognini D, Rock E M, Cluny N L, Cascio M G, Limebeer C L, Duncan M et al. (2013). Cannabidiolic acid prevents vomiting in Suncus murinus and nausea-induced behaviour in rats by enhancing $5-HT_{1A}$ receptor activation. Br J Pharmacol 168: 1456-1470.

Campos A C, Guimarães F S (2008). Involvement of $5HT_{1A}$ receptors in the anxiolytic-like effects of cannabidiol injected into the dorsolateral periaqueductal gray of rats. Psychopharmacology (Berl) 199: 223-230.

Cascio M G, Pertwee R G (2014). Known pharmacological actions of nine non-psychotropic phytocannabinoids. In: Pertwee R G (ed). Handbook of Cannabis. Oxford University Press: Oxford, pp. 137-156.

Cascio M G, Gauson L A, Stevenson L A, Ross R A, Pertwee R G (2010). Evidence that the plant cannabinoid cannabigerol is a highly potent α2-adrenoceptor agonist and moderately potent $5HT_{1A}$ receptor antagonist. Br J Pharmacol 159: 129-141.

Christopoulos A, Changeux J-P, Catterall W A, Fabbro D, Burris T P, Cidlowski J A et al. (2014). International Union of Basic and Clinical Pharmacology. XC. Multisite pharmacology: recommendations for the nomenclature of receptor allosterism and allosteric ligands. Pharmacol Rev 66: 918-947.

Crombie L, Crombie W M L (1977). Cannabinoid acids and esters: miniaturized synthesis and chromatographic study. Phytochemistry 16: 1413-1420.

Curtis M J, Bond R A, Spina D, Ahluwalia A, Alexander S P, Giembycz M A et al. (2015). Experimental design and analysis and their reporting: new guidance for publication in BJP. Br J Pharmacol 172: 3461-3471.

Grill H J, Norgren R (1978). Chronically decerebrate rats demonstrate satiation but not bait shyness. Science 201: 267-269.

Kilkenny C, Browne W, Cuthill I C, Emerson M, Altman D G (2010). NC3Rs Reporting Guidelines Working Group. Br J Pharmacol 160: 1577-1579.

Krejčí Z, Šantavý F (1955). Isolace dals'ich látek z listí indického konopí Cannabis sativa L. Acta Univ Palacki Olomuc 6: 59-66.

Laprairie R B, Bagher A M, Kelly M E, Denovan-Wright E M (2015). Cannabidiol is a negative allosteric modulator of the cannabinoid CB1 receptor. Br J Pharmacol 172: 4790-4805.

Limebeer C L, Vemuri V K, Bedard H, Lang S T, Ossenkopp K P, Makriyannis A et al. (2010). Inverse agonism of cannabinoid CB1 receptors potentiates LiCl-induced nausea in the conditioned gaping model in rats. Br J Pharmacol 161: 336-349.

McGrath J C, Lilley E (2015). Implementing guidelines on reporting research using animals (ARRIVE etc.): new requirements for publication in BJP. Br J Pharmacol 172: 3189-3193.

Mechoulam R (1973). Cannabinoid chemistry. In: Marijuana Chemistry, Metabolism, Pharmacology and Clinical Effects. Ed Mechoulam R Academic Press: New York, pp. 1-99.

Mechoulam R, Ben-Zvi Z (1969). Carboxylation of rescorcinols and methyl magnesium carbonate. Synthesis of cannabinoid acids. J Chem Soc D—Chem Commun Issue 7: 343-344.

Mechoulam R, Gaoni Y (1965). Hashish-IV. The isolation and structure of cannabinolic, cannabidiolic and cannabigerolic acids. Tetrahedron 21: 1223-1229.

Mechoulam R, Parker L A, Gallily R (2002). Cannabidiol: an overview of some pharmacological aspects. J Clin Pharmacol 42: 11S-19S.

Norman R O C, Coxon J M (1993). Principles of organic synthesis. Blackie Academic: London, p. 389.

Patel S, Hill M N, Cheer J F, Wotjak C T, Holmes A (2017). The endocannabinoid system as a target for novel anxiolytic drugs. Neurosci Biobehav Rev 76: 56-66.

Rock E M, Bolognini D, Limebeer C L, Cascio M G, Anavi-Goffer S, Fletcher P J et al. (2012). Cannabidiol, a non-psychotropic component of cannabis, attenuates vomiting and nausea-like behaviour via indirect agonism of 5-HT1A somatodendritic autoreceptors in the dorsal raphe nucleus. Br J Pharmacol 165: 2620-2634.

Rock E M, Parker L A (2013). Effect of low doses of cannabidiolic acid and ondansetron on LiCl-induced conditioned gaping (a model of nausea-induced behaviour) in rats. Br J Pharmacol 169: 685-692.

Rock E M, Parker L A (2015). Synergy between cannabidiol, cannabidiolic acid, and Δ9-tetrahydrocannabinol in the regulation of emesis in the Suncus murinus (house musk shrew). Behav Neurosci 129: 368-370.

Rock E M, Limebeer C L, Navaratnam R, Sticht M A, Bonner N, Engeland K et al. (2014). A comparison of cannabidiolic acid with other treatments for anticipatory nausea using a rat model of contextually elicited conditioned gaping. Psychopharmacology (Berl) 231: 3207-3215.

Rock E M, Limebeer C L, Parker L A (2015). Effect of combined doses of Δ9-tetrahydrocannabinol (THC) and cannabidiolic acid (CBDA) on acute and anticipatory nausea using rat (Sprague-Dawley) models of conditioned gaping. Psychopharmacology (Berl) 232: 4445-4454.

Rock E M, Connolly C, Limebeer C L, Parker L A (2016). Effect of combined oral doses of Δ9-tetrahydrocannabinol (THC) and cannabidiolic acid (CBDA) on acute and anticipatory nausea in rat models. Psychopharmacology (Berl) 233: 3353-3360.

Rock E M, Limebeer C L, Petrie G N, Williams L A, Mechoulam R, Parker L A (2017). Effect of prior foot shock stress and Δ9-tetrahydrocannabinol, cannabidiolic acid, and cannabidiol on anxiety-like responding in the light-dark emergence test in rats. Psychopharmacology (Berl) 234: 2207-2217.

Southan C, Sharman J L, Benson H E, Faccenda E, Pawson A J, Alexander S P H et al. (2016). The IUPHAR/BPS guide to PHARMACOLOGY in 2016: towards curated quantitative interactions between 1300 protein targets and 6000 ligands. Nucl Acids Res 44: D1054-D1068.

Takeda S, Okazaki H, Ikeda E, Abe S, Yoshioka Y, Watanabe K et al. (2014). Down-regulation of cyclooxygenase-2 (COX-2) by cannabidiolic acid in human breast cancer cells. J Toxicol Sci 39: 711-716.

Takeda S, Himeno T, Kakizoe K, Okazaki H, Okada T, Watanabe K et al. (2017). Cannadidiolic acid-mediated selective down-regulation of c-fos in highly aggressive breast cancer MDA-MB-231 cells: possible involvement of its down-regulation in the abrogation of aggressiveness. J Nat Med 71: 286-291.

Zhornitsky S, Potvin S (2012). Cannabidiol in humans—the quest for therapeutic targets. Pharmaceuticals 21: 529-552.

Zuardi A W, Cosme R A, Graeff F G, Guimarães FS (1993). Effect of ipsapirone and cannabidiol on human experimental anxiety. J Psychopharmacol 7: 82-88.

What is claimed is:

1. A method of treating a subject suffering from anxiety comprising administering an effective amount of a compound of formula (I) to the subject:

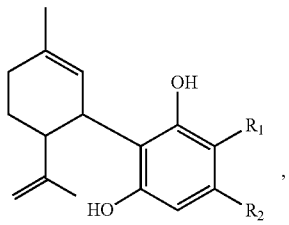

wherein $R_1$ is —C(=O)$OR_3$, $R_3$ is $CH_3$ and $R_2$ is straight $C_5$ alkyl, wherein the method does not include administering the compound of formula I wherein $R_3$ is a straight or branched $C_2$-$C_{15}$ alkyl, does not include administering the compound of formula I wherein $R_3$ is a straight or branched $C_2$-$C_{15}$ alkenyl, and does not include administering the compound of formula I wherein $R_3$ is straight or branched $C_2$-$C_{15}$ alkynyl.

2. The method of claim 1, wherein the compound is administered orally, nasally, topically, parenterally, or via an implant.

3. The method of claim 1, wherein the compound is administered orally.

4. The method of claim 1, wherein the compound is administered in a pharmaceutical composition in the form of a pill, a tablet, a dragee, a capsule, a powder, a granule, a solution, or a suspension.

5. The method of claim 4, wherein the pharmaceutical composition comprises an auxiliary agent selected from the group consisting of a carrier, a filler, a binder, a diluent, a disintegrant, a lubricant, a colorant, a flavoring agent, an anti-oxidant, and a wetting agent.

6. The method of claim 4, wherein the pharmaceutical composition comprises an additional therapeutic agent.

7. The method of claim 1, wherein the subject suffers from stress-induced anxiety.

* * * * *